United States Patent [19]

Cugnon de Sevricourt et al.

[11] Patent Number: 5,648,381
[45] Date of Patent: Jul. 15, 1997

[54] DERIVATIVES OF INDAN-1,3-DIONE AND INDAN-1,2,3-TRIONE, METHODS OF PREPARING THEM AND THERAPEUTIC USE THEREOF

[75] Inventors: Michel P. Cugnon de Sevricourt, Moult; Catherine G. Dacquet, Paris; Michel A. Finet, Fresnes; Florence J. Le Marquer; Max F. Robba, both of Paris; Norbert O. Tembo, Cergy St. Christophe; Sylvie J. Yannic-Arnoult, Grigny; Jean-Luc Torregrosa, Saint-Denis, all of France

[73] Assignee: Innothera, Arcueil, France

[21] Appl. No.: 142,478

[22] PCT Filed: Apr. 1, 1993

[86] PCT No.: PCT/FR93/00329

§ 371 Date: Mar. 24, 1994

§ 102(e) Date: Mar. 24, 1994

[87] PCT Pub. No.: WO93/20046

PCT Pub. Date: Oct. 14, 1993

[30] Foreign Application Priority Data

Apr. 3, 1992 [FR] France ............................ 92 04071

[51] Int. Cl.[6] .................................................. C07D 213/87
[52] U.S. Cl. .................................... 514/471; 549/487
[58] Field of Search ............................. 549/487; 514/471

[56] References Cited

U.S. PATENT DOCUMENTS 3,280,185  10/1966  Wendt et al. ......................... 549/487

FOREIGN PATENT DOCUMENTS

| 0172128 | 2/1986 | European Pat. Off. . |
| 0236151 | 9/1987 | European Pat. Off. . |
| 0456133 | 11/1991 | European Pat. Off. . |
| 2127982 | 12/1972 | Germany . |

*Primary Examiner*—Jacqueline Haley
*Attorney, Agent, or Firm*—Finnegan, Henderson, Farabow, Garrett & Dunner

[57] ABSTRACT

Compounds of use in therapy and having the formula:

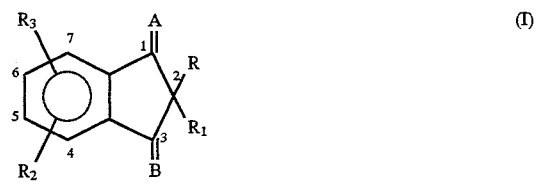

in which $R_2$ and $R_3$ independently denote H, $C_1$–$C_4$ alkoxy or OH and (A, B)=(oxygen, oxygen) in which case one out of R and $R_1$ denotes OH, halogen, secondary amino or tertiary amine and the other denotes $NHCOR_4$, $NHNHCOR_5$ or $NHNHCOCONH_2$, or R and $R_1$ together form =N—NH—CO—R'$_5$, =N—NH—CO—CO—$NH_2$, (=N—NH—$R_6$, =N—$R_7$, =N—O—CO—$R_8$ or =C($CH_3$)—NH—NH—CO—$R_9$; or (A, B) =(N—NH—CX—$NHR_{10}$, oxygen) in which case R and $R_1$ together form =N—OH.

5 Claims, No Drawings

DERIVATIVES OF INDAN-1,3-DIONE AND INDAN-1,2,3-TRIONE, METHODS OF PREPARING THEM AND THERAPEUTIC USE THEREOF

This is a National Stage application of PCT/FR93/00329 filed 1. Apr. 1993 and published as WO 93/20046 on 14 Oct. 1993.

The invention relates to novel derivatives of indan-1,2-dione and indan-1,2,3-trione, methods of preparation thereof and use thereof in therapy.

More specifically, these derivatives have the formula:

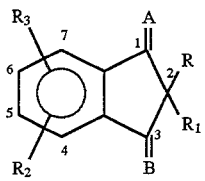
(I)

in which $R_2$ and $R_3$ independently denote H, $C_1-C_4$ alkoxy or OH, and the pair (A, B) denotes either:

(oxygen, oxygen), in which case one out of R and $R_1$ denotes OH, halogen, ($C_1-C_4$ alkyl) NH, N-morpholino($C_1-C_4$ alkyl) NH, 1-(pyridyl)-4-piperazino or 1-(phenyl)-4-piperazino in which the phenyl ring is optionally substituted by a halogen, and the other denotes a group chosen from among the following:

$NHCOR_4$ where $R_4$=phenyl, $C_1-C_4$ alkyl or $C_1-C_4$ alkyl substituted by a halogen, $NHNHCOR_5$ where $R_5$=$C_1-C_4$ alkoxy; phenyl, phenyl substituted by one or two groups chosen from among the following: amino, $C_1-C_4$ alkoxy, $C_1-C_4$ alkyl or OH; thienyl; furyl; pyridyl; indolyl-2-methyl; indolyl-3-methyl; or 5-phenyl-2-(N-pyrrolyl)thienyl, or $NHNHCOCONH_2$, excluding derivatives in which one out of R and $R_1$ represents OH or halogen and the other represents $NHCOR_4$ where $R_4$=phenyl or $C_1-C_4$ alkyl; derivatives in which one out of R and $R_1$ denotes ($C_1-C_4$ alkyl)NH and the other denotes $NHCOR_4$ where $R_4$=$C_1-C_4$ alkyl; and derivatives in which one out of R and $R_1$ denotes OH and the other denotes $NHNHCOR_5$ where $R_5$=pyridyl or phenyl substituted by a $C_1-C_4$ alkoxy group, and R and $R_1$ may also together form a group, i.e.:
=NNHCOR'$_5$ where R'$_5$=$R_5$, trifluoroacetylaminophenyl, acetylaminophenyl, pyrazinyl or pyrrolyl,
=NNHCOCONH$_2$,
=NNHR$_6$ where $R_6$=phenyl; phenyl substituted by one or two groups chosen from among $C_1-C_4$ alkyl, halogen and $C_1-C_4$ alkoxy; methyl sulphonyl phenyl; or N-methyl methane sulphanomidophenyl,
=N—$R_7$ where $R_7$=phenyl or phenyl substituted by an OH group,
=N—O—CO—$R_8$ where $R_8$=phenyl or phenyl substituted by a halogen atom or
=C($CH_3$)—NH—NH—CO—$R_9$ where $R_9$=phenyl, phenyl amino, phenyl substituted by a halogen atom or an OH group, or phenylamino substituted by a halogen atom or an OH group, excepting derivatives in which R and $R_1$ together form an =NNHCOR'$_5$ group where R'$_5$=pyridyl or phenyl substituted by $C_1-C_4$ alkoxy and derivatives in which R and $R_1$ together form an =N—NHR$_6$ group where $R_6$=phenyl or phenyl substituted by a halogen atom or a $C_1-C_4$ alkyl or alkoxy group; or (NNHCXNHR$_{10}$, oxygen) where X denotes oxygen or sulphur and $R_{10}$=H, phenyl or phenyl substituted by one or two groups chosen from among OH, $CF_3$, $C_1-C_4$ alkyl, $C_1-C_4$ alkoxy, halogen, methylene dioxy, acetoxy and hydroxyethyl, in which case R and $R_1$ together form an =N—OH group.

Formula (I) hereinbefore includes:

(i) compounds having the formula:

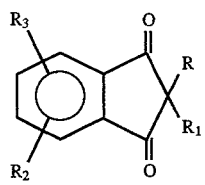
(I')

where R, $R_1$, $R_2$ and $R_3$ have the same meanings as in formula (I) when the pair (A, B) therein denotes (oxygen, oxygen), and (ii) compounds having the formula:

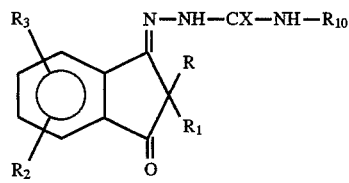
(I")

where, R, $R_1$, $R_2$, $R_3$, X and $R_{10}$ have the same meanings as in formula (I), when the pair (A, B) therein denotes (=NNHCXNHR$_{10}$, oxygen).

Formula (I) hereinbefore includes:

(a) compounds having the following formula:

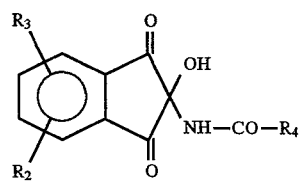
(Io)

where $R_4$=$C_1-C_4$ alkyl substituted by a halogen.

(b) compounds having the following formula:

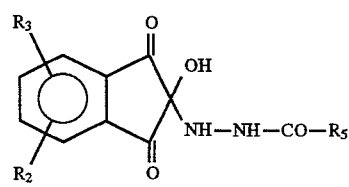
(Ia)

where $R_5 \neq$ pyridyl and phenyl substituted by a $C_1-C_4$ alkoxy group.

(c) compounds having the formula:

(Ib)

[structure: indane-1,3-dione with R3, R2 on benzene ring; at 2-position: OH and NH—NH—CO—CO—NH2]

(d) compounds having the formula:

(I'o)

[structure: indane-1,3-dione with R3, R2 on benzene ring; at 2-position: Halogen and NHCOR4]

where $R_4 = C_1-C_4$ alkyl substituted by a halogen.

(e) compounds having the formula:

(Ic)

[structure: indane-1,3-dione with R3, R2; at 2-position: Halogen and NH—NH—CO—R5]

(f) compounds having the formula:

(Id)

[structure: indane-1,3-dione with R3, R2; at 2-position: Halogen and NH—NH—CO—CO—NH2]

(g) compounds having the formula:

(Ie)

[structure: indane-1,3-dione with R3, R2; at 2-position: R and R1]

where one out of R and $R_1$ denotes NHCOR4 and the other denotes ($C_1-C_4$ alkyl) NH, N-morpholino ($C_1-C_4$ alkyl) NH, 1-(pyridyl)-4-piperazino or 1-(phenyl)-4-piperazino in which the phenyl ring is optionally substituted by a halogen, except for compounds in which one out of R and $R_1$ denotes NHCOR4 where $R_4 = C_1-C_4$ alkyl and the other denotes ($C_1-C_4$ alkyl) NH.

(h) compounds having the formula:

(If)

[structure: indane-1,3-dione with R3, R2; at 2-position: R and R1]

where one out of R and $R_1$ denotes NHNHCOR5 and the other denotes ($C_1-C_4$ alkyl) NH, N-morpholino ($C_1-C_4$ alkyl), NH, 1-(pyridyl)-4-piperazino or 1-(phenyl)-4-piperazino in which the phenyl ring is optionally substituted by a halogen.

(i) compounds having the formula:

(Ig)

[structure: indane-1,3-dione with R3, R2; at 2-position: R and R1]

where one out of R and $R_1$ denotes NHNHCOCONH2 and the other denotes ($C_1-C_4$ alkyl) NH, morpholino ($C_1-C_4$ alkyl) NH, 1-(pyridyl)-4-piperazino or 1-(phenyl)-4-piperazino in which the phenyl ring is optionally substituted by a halogen.

(j) compounds having the formula:

(Ih)

[structure: indane-1,3-dione with R3, R2; at 2-position: =N—NH—CO—R5']

apart from those in which $R'_5$=phenyl substituted by $C_1-C_4$ alkoxy; or pyridyl.

(k) compounds having the formula:

(Ii)

[structure: indane-1,3-dione with R3, R2; at 2-position: =N—NH—CO—CO—NH2]

(l) compounds having the formula:

(Ij)

[structure: indane-1,3-dione with R3, R2; at 2-position: =N—NH—R6]

except for compounds in which $R_6$=phenyl or phenyl substituted by a halogen atom or a $C_1-C_4$ alkyl or alkoxy group.

(m) compounds having the formula:

(Ik)

[structure: indane-1,3-dione with R3, R2; at 2-position: =N—R7]

(n) compounds having the formula:

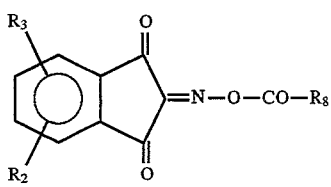
(II)

(o) compounds having the formula:

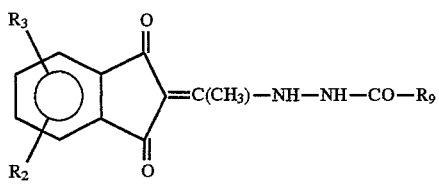
(Im)

(p) compounds having the formula:

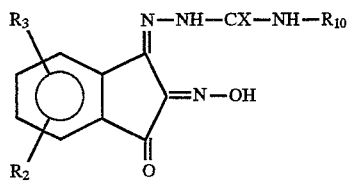
(In)

the symbols $R_1$, $R_3$, $R_5$, $R'_5$, $R_6$, $R_7$, $R_8$, $R_9$, $R_{10}$ and X having the same meanings as in formula (I).

In formulae (I') and (I") and (Ia) to (In) hereinbefore, $R_2$ is inter alia in position 5 and $R_3$ in position 6.

Also, in formulae (I') and (I") and (Ia) to (In), the pair ($R_2$, $R_3$) may inter alia be (H, H), (5-OCH$_3$,H), (5-OH, H) or (5-OCH$_3$, 6-OCH$_3$).

The invention also covers salts of the salt-forming compounds among those described hereinbefore. These salts comprise addition salts of mineral acids such as hydrochloric, hydrobromic, sulphuric or phosphoric acid, and addition salts of organic acids such as acetic, propionic, oxalic or citric acid.

The invention also covers all possible stereoisomers of formula (I) derivatives and mixtures of such stereoisomers, as well as the metabolites of these derivatives.

The invention also covers methods of preparing formula (I) derivatives. These methods are described in diagrams 1 to 5 hereinafter, in which the symbols R to $R_{10}$ and X, unless stated otherwise, have the same meanings as in formula (I).

Diagram 1

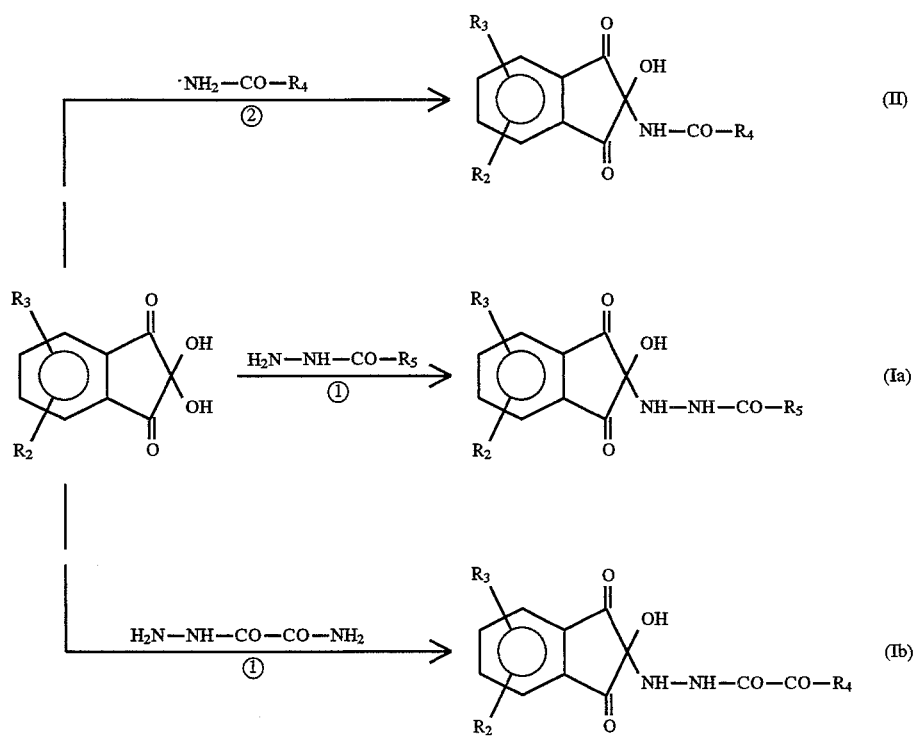

-continued
Diagram 2
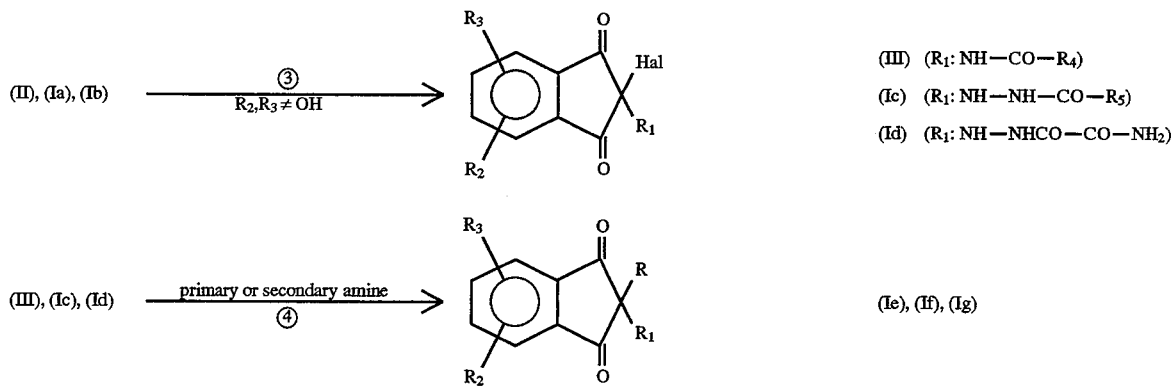
Diagram 3
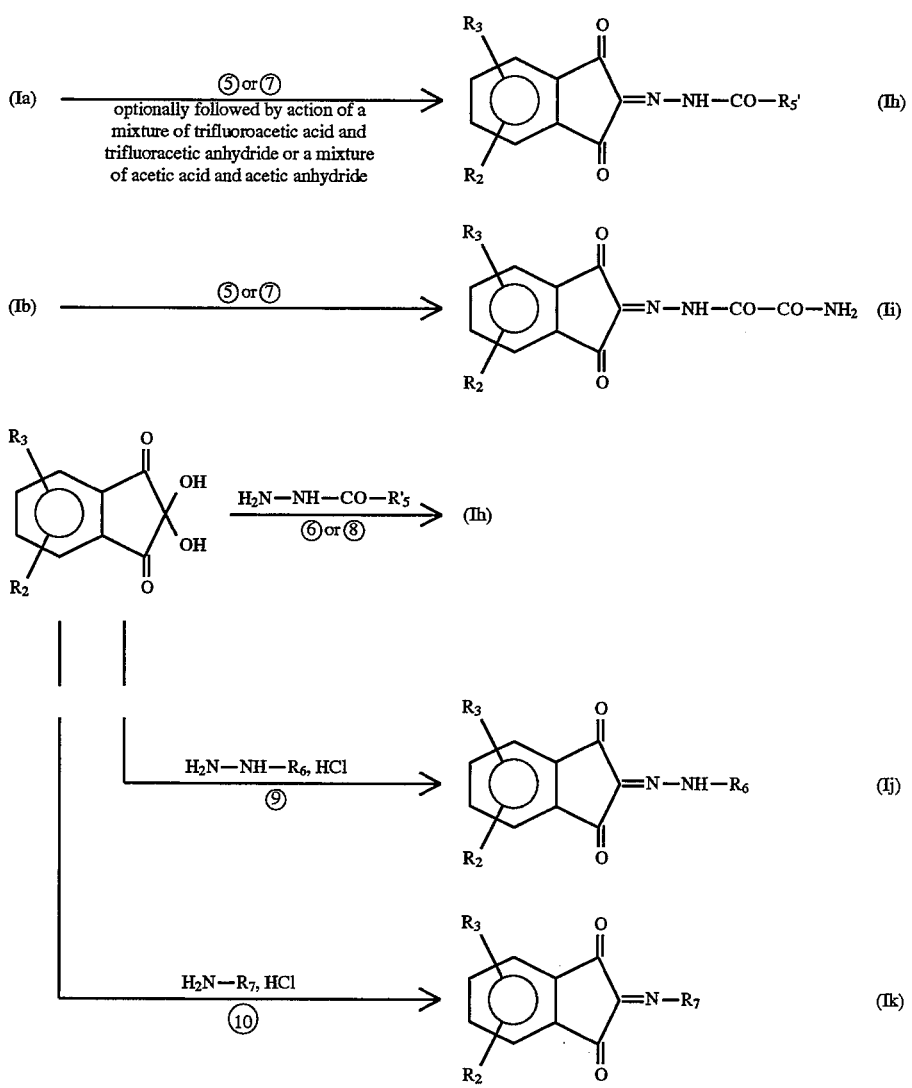

-continued
Diagram 4

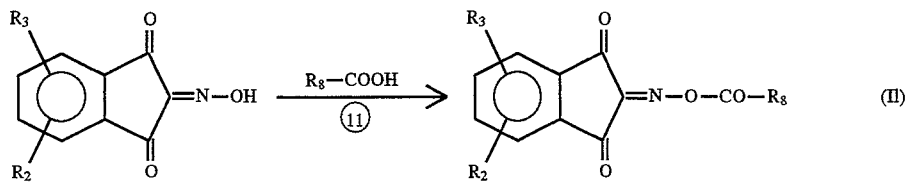

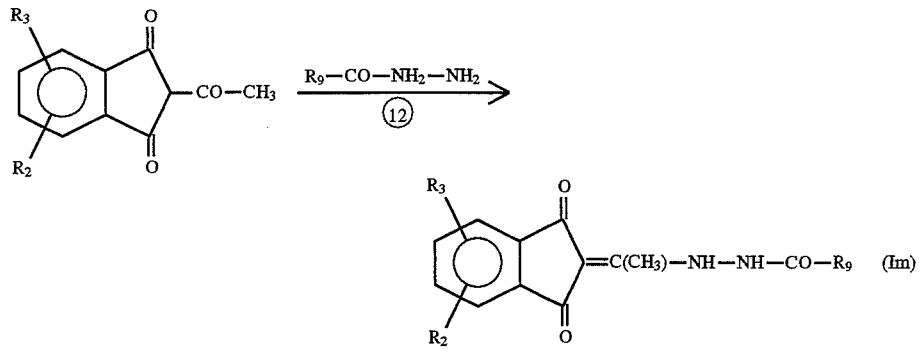

Diagram 5

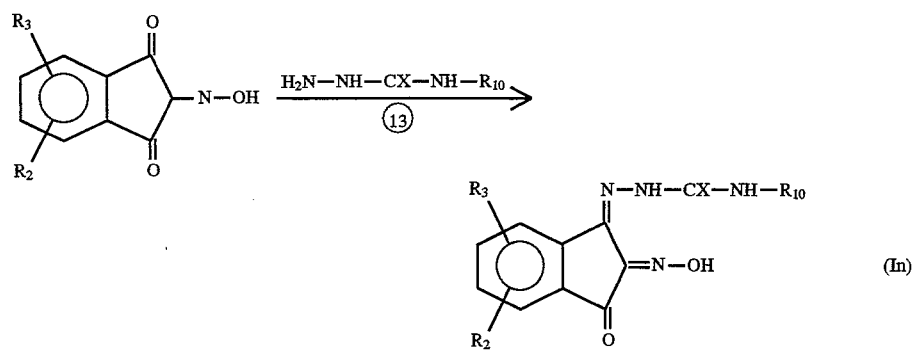

In the diagrams hereinbefore, ① to ⑬ denote the methods used and have the following meanings:

① Condensation in a solvent such as ethanol, hot and preferably refluxed.
② Condensation in a solvent such as benzene, hot and preferably refluxed.
③ Reaction with a halogenating agent, inter alia a chlorinating agent, preferably thionyl chloride, in a solvent such as THF, hot and preferably refluxed.
④ Condensation with a primary amine [($C_1$–$C_4$ alkyl) $NH_2$ or N-morpholino ($C_1$–$C_4$ alkyl) $NH_2$] or a secondary amine [1-(pyridyl)-4-piperazine or 1-(phenyl)-4-piperazine in which the phenyl ring is optionally substituted by a halogen atom] in a solvent such as diethyl ether, in the presence of a base such as triethyl amine.
⑤ Treatment when hot, preferably with reflux, in ethanol and in the presence of concentrated HCl.
⑥ Condensation when hot, preferably with reflux, in a solvent such as ethanol and in the presence of concentrated HCl.
⑦ Heating, preferably with reflux, of a suspension of (Ia) or (Ib) in acetonitrile.
⑧ Condensation when hot, preferably with reflux, in a solvent such as ethanol.
⑨ Condensation when hot preferably with reflux in a solvent such as aqueous ethanol.
⑩ Condensation when hot preferably with reflux in a solvent such as aqueous ethanol.
⑪ Condensation of isobutyl chloroformate on $R_8$—COOH, inter alia in a solvent such as ethyl acetate and in the presence of a base such as N-methyl morpholine; the resulting mixed anhydride is then condensed with hydroxy imine.
⑫ Condensation, inter alia in a solvent, preferably ethanol, preferably with reflux.
⑬ Condensation of the semicarbazide or thiosemicarbazide in hydrochloride form, inter alia in a solvent such as aqueous ethanol, advantageously hot and preferably refluxed.

The salts of the salt-forming compounds among those having formula (I) may be obtained e.g. by action of an acid on the salt-forming compound in solution in a suitable organic solvent.

The following preparations are given by way of example to illustrate the invention.

A/ Preparation of the raw materials

Example a 5-hydroxyindan-1,3-dione 4 ml of 10N sulphuric acid were added to a suspension of 0.01 mol of 5-acetoxy-2-carbethoxy-3-hydroxy-1-indanone in 80 ml water. The reaction mixture was refluxed for 15 minutes. The insoluble substance was filtered when hot and the yellow precipitate formed after cooling was dried on suction pump, washed in ice water and dried.

Yield: 85%; M.P.: 208° C.; IR: ν OH=3250 cm$^{-1}$, ν CO=1730 and 1680 cm$^{-1}$.

Example b 2-bromo-5-hydroxyindan-1,3-dione 0.02 mol bromine was added dropwise to a solution of 0.02 mol of 5-hydroxyindan-1,3-dione in 60 ml chloroform. The reaction mixture was agitated at 50° C. for 30 minutes and the precipitate obtained after evaporation of the solvent was recrystallised.

Yield: 60%; M.P.: 194° C.; IR: ν OH=3380 cm$^{-1}$, ν CO=1740 and 1710 cm$^{-1}$.

Recrystallisation solvent: a mixture (V/V) of ethyl ether and petroleum ether.

Example c 5-hydroxyindan-1,2,3-trione, monohydrate

A solution of 0.01 mol of 2-bromo-5-hydroxyindan-1,3-dione in 10 ml dimethyl sulphoxide was heated to 80° C. for 30 minutes. 50 ml of a 1N hydrochloric acid solution was added, after which heating was continued for 30 minutes. The oily suspension obtained after cooling was extracted with ethyl ether. The organic phase was washed in water and dried over magnesium sulphate.

The yellow precipitate obtained after evaporation of the solvent was recrystallised from water.

Yield: 45%; M.P.: >265° C.; IR: ν OH=3340 cm$^{-1}$, ν CO=1750 and 1710 cm$^{-1}$.

Example d 5,6-dimethoxyindan-1,2,3-trione, monohydrate 0.06 mol of selenium oxide in solution in 2.5 ml water was added to a solution of 0.03 mol of 5,6-dimethoxy-1-indanone in 100 ml dioxan. The reaction mixture was refluxed for 7 hours and the residue obtained after evaporation of the solvent was dissolved in ethyl acetate. The organic phase was washed several times in water, dried over magnesium sulphate and decolorized.

The precipitate obtained after evaporation of the solvent was recrystallised from ethyl ether.

Yield: 50%; M.P.: 170° C.; IR: ν CO=1730 and 1700 cm$^{-1}$.

Example e 6-hydroxy-5-methoxyindan-1,2,3-trione, monohydrate 0.06 mol of selenium oxide in solution in 2.5 ml water was added to a solution of 0.03 mol of 6-hydroxy-5-methoxy-1-indanone in 100 ml dioxan. The reaction mixture was refluxed for 7 hours and the residue obtained after evaporation of the solvent was dissolved in ethyl acetate. The organic phase was washed several times in water, dried over magnesium sulphate and decolorized.

The precipitate obtained after evaporation of the solvent was recrystallised from water.

Yield: 50%; M.P.>265° C.; IR: ν CO=1740 and 1700 cm$^{-1}$.

Example f 2-oximino-5-hydroxyindan-1,3-dione 0.02 mol of sodium nitrite in solution in 8 ml water was added dropwise, keeping the temperature at 5° C., to a suspension of 0.01 mol of 5-hydroxyindan-1,3-dione in 6 ml of 2N sulphuric acid solution. The reaction mixture was agitated at 5° C. for 4 hours. The insoluble substance was dried on suction pump, washed in water, dried and recrystallised from acetone.

Yield: 65%; M.P. 220° C.; IR: ν OH=3400 and 3260 cm$^{-1}$, ν CO=1730 and 1690 cm$^{-1}$.

Reference hereinafter is made indifferently to ninhydrin, indan-1,2,3-trione monohydrate and 2,2-dihydroxy-1,3-dioxo-2H-indene.

B/ Preparation of formula (Ia)–(Id), (II) and (III) compounds

Method ①

0.01 mol of H$_2$N—NH—CO—R$_5$ or H$_2$N—NH—CO—CO—NH$_2$ in solution in 20 ml ethanol was added to a solution of 0.01 mol ninhydrin in 20 ml ethanol.

The reaction mixture was heated to 60° C. for 5 to 15 minutes and the resulting white precipitate was dried on suction pump, washed in ethyl ether and dried.

Method ②

0.04 mol of NH$_2$—CO—R$_4$ was added to a solution of 0.04 mol ninhydrin in 40 ml benzene. The reaction mixture was refluxed for an hour. The white precipitate formed after cooling in an ice bath was dried on suction pump and dissolved in 150 ml of ethyl ether. The organic phase was washed three times with 100 ml water and dried over magnesium sulphate. The white crystals formed after evaporation of the solvent were recrystallised.

Method ③

3.5 ml (0.04 mol) of thionyl chloride were added dropwise to a solution of 6 g (0.02 mol) of 2-benzamido-2-hydroxyindan-1,3-dione in 20 ml of tetrahydrofuran. The reaction mixture was refluxed for an hour. The residual oil obtained after evaporating the excess thionyl chloride and tetrahydrofuran crystallised after washing with petroleum ether.

EXAMPLE 1

2-hydroxy-2-methoxycarbonyl hydrazinoindan-1,3-dione

Method ①

Raw materials: indan-1,2,3-trione monohydrate methoxycarbonyl hydrazine

Yield: 90%; M.P.: 188° C.; IR: ν OH=3360 cm$^{-1}$, ν NH=3260 cm$^{-1}$, ν CO=1760 and 1700 cm$^{-1}$.

EXAMPLE 2

2-hydroxy-2-methoxycarbonyl hydrazino-5-methoxyindan-1,3-dione

Method ①

Raw materials: 5-methoxyindan-1,2,3-trione monohydrate methoxycarbonyl hydrazine Yield: 81%; M.P.: 190° C.; IR: ν OH=3360 cm$^{-1}$, ν NH=3270 cm$^{-1}$, ν CO=1760 and 1720 cm$^{-1}$.

EXAMPLE 3

2-benzoyl hydrazino-2-hydroxy-indan-1,3-dione

Method ①

Raw materials: indan-1,2,3-trione monohydrate benzoylhydrazine

Yield: 93%; M.P.: 188° C.; IR: ν OH=3320 cm$^{-1}$, ν NH=3240 cm$^{-1}$, ν CO=1750, 1720 and 1640 cm$^{-1}$.

EXAMPLE 4

2-benzoyl hydrazino-2-hydroxy-5-methoxyindan-1,3-dione

Method ①

Raw materials: 5-methoxyindan-1,2,3-trione monohydrate benzoyl hydrazine

Yield: 93%; M.P.: 180° C.; IR: ν OH=3350 cm$^{-1}$, ν NH=3250 cm$^{-1}$, ν CO=1750, 1720 and 1650 cm$^{-1}$.

EXAMPLE 5

2-hydroxy-2-(3-methoxybenzoylhydrazino)-5-methoxyindan-1,3-dione

Method ①

Raw materials: 5-methoxyindan-1,2,3-trione monohydrate 3-methoxybenzoylhydrazine Yield: 85%; M.P.: 178° C.; IR: ν OH=3360 cm$^{-1}$, ν NH=3250 cm$^{-1}$, ν CO=1760, 1720 and 1650 cm$^{-1}$.

EXAMPLE 6

2-hydroxy-2-(2-methylbenzoylhydrazino)-indan-1,3-dione

Method ①

Raw materials: Indan-1,2,3-trione monohydrate 2-methylbenzoylhydrazine

Yield: 98%; M.P.: 192° C.; IR: ν OH=3300 cm$^{-1}$, ν NH=3220 cm$^{-1}$, ν CO=1750, 1720 and 1630 cm$^{-1}$.

EXAMPLE 7

2-hydroxy-2-(3-methylbenzoylhydrazino)-indan-1,3-dione

Method ①

Raw materials: Indan-1,2,3-trione monohydrate 3-methylbenzoylhydrazine

Yield: 98%; M.P.: 184° C.; IR: ν OH=3360 cm$^{-1}$, ν NH=3160 cm$^{-1}$, ν CO=1740, 1700 and 1640 cm$^{-1}$.

EXAMPLE 8

2-hydroxy-2-(4-methylbenzoylhydrazino)-indan-1,3-dione

Method ①

Raw materials: indan-1,2,3-trione monohydrate 4-methylbenzoylhydrazine

Yield: 98%; M.P.: 200° C.; IR: ν OH=3340 cm$^{-1}$, ν NH=3220 cm$^{-1}$, ν CO=1750, 1720 and 1630 cm$^{-1}$.

EXAMPLE 9

2-hydroxy-2-(2-hydroxybenzoylhydrazino)-indan-1,3-dione

Method ①

Raw materials: Indan-1,2,3-trione monohydrate 2-hydroxybenzoylhydrazine

Yield: 98%; M.P.: 170° C.; IR: ν OH=3350 cm$^{-1}$, ν NH=3220 cm$^{-1}$, ν CO=1760, 1720 and 1640 cm$^{-1}$.

EXAMPLE 10

2-hydroxy-2-(3-hydroxybenzoylhydrazino)-indan-1,3-dione

Method ①

Raw materials: Indan-1,2,3-trione monohydrate 3-hydroxybenzoylhydrazine

Yield: 98%; M.P.: 210° C.; IR: ν OH=3350 cm$^{-1}$, ν NH=3220 cm$^{-1}$, ν CO=1760, 1720 and 1640 cm$^{-1}$.

EXAMPLE 11

2-(3,4-dimethoxybenzoylhydrazino)-2-hydroxyindan-1,3-dione

Method ①

Raw materials: Indan-1,2,3-trione monohydrate 3,4-dimethoxybenzoylhydrazine

Yield: 90%; M.P.: 210° C.; IR: ν OH=3360 cm$^{-1}$, ν NH=3250 cm$^{-1}$, ν CO=1760, 1730 and 1630 cm$^{-1}$.

EXAMPLE 12

2-hydroxy-2-(2-hydroxy-3-methylbenzoythydrazino)-indan-1,3-dione

Method ①

Raw materials: Indan-1,2,3-trione monohydrate 2-hydroxy-3-methylbenzoylhydrazine Yield: 98%; M P.: 216° C.; IR: ν OH=3360 cm$^{-1}$, ν NH=3240 cm$^{-1}$, ν CO=1760, 1720 and 1635 cm$^{-1}$.

EXAMPLE 13

2-hydroxy-2-(4-hydroxy-3-methoxybenzoylhydrazino)-indan-1,3-dione

Method ①

Raw materials: Indan-1,2,3-trione monohydrate 4-hydroxy-3-methoxybenzoylhydrazine Yield: 98%; M.P.: 236° C.; IR: ν OH=3350 cm$^{-1}$, ν NH=3220 cm$^{-1}$, ν CO=1750, 1720 and 1635 cm$^{-1}$.

EXAMPLE 14

2-hydroxy-2-(5-phenyl-2-N-pyrrolyl)thiophene-3-carbonylhydrazino)-indan-1,3-dione Method ①

Raw materials: Indan-1,2,3-trione monohydrate 5-phenyl-2-(N-pyrrolyl)thiophene-3-carbonylhydrazine Yield: 90%; M.P.: 200° C.; IR: ν OH=3300 cm$^{-1}$, ν NH=3200 cm$^{-1}$, ν CO=1730, 1700 and 1625 cm$^{-1}$.

EXAMPLE 15

2-hydroxy-2-oxamoyl hydrazinoindan-1,3-dione

Method ①

Raw materials: Indan-1,2,3-trione monohydrate oxamoyl hydrazine

Yield: 95%; M.P.: 260° C.; IR: ν OH=3420 cm$^{-1}$, ν NH=3300, 3200 and 3100 cm$^{-1}$, ν CO=1760, 1720 and 1670 cm$^{-1}$.

EXAMPLE 16

2-hydroxy-2-(indole-3-acetyl hydrazino)-indan-1,3-dione

Method ①

Raw materials: Indan-1,2,3-trione monohydrate indole-3-acetyl hydrazine

Yield: 90%; M.P.: 204° C.; IR: ν OH=3350 cm$^{-1}$, ν NH=3225 cm$^{-1}$, ν CO=1720 and 1680 cm$^{-1}$.

EXAMPLE 17

2-chloroacetamido-2-hydroxyindan-1,3-dione

Method ②

Raw materials: Indan-1,2,3-trione monohydrate 2-chloroacetamide

Yield: 85%; M.P.: 164° C.; IR: ν OH=3380 cm$^{-1}$, ν NH=3180 cm$^{-1}$, ν CO=1765, 1730 and 1640 cm$^{-1}$.

Recrystallisation solvent: ethyl ether

EXAMPLE 18

2-(4-aminobenzoylhydrazino)-2-hydroxy-indan-1,3-dione

Method ①

Raw materials: ninhydrin; 4-aminobenzoyl hydrazine

Yield: 80%; M.P.: 220° C.; IR: ν OH=3440 cm$^{-1}$, ν NH=3340 and 3220 cm$^{-1}$, ν CO=1750 and 1720 cm$^{-1}$.

C/ Preparation of compounds having the formulae (Ie)–(Ig)
Method ④

1 ml of triethylamine was added to a solution of 0.007 mol of 2-benzamido-2-chloroindan-1,3-dione in 60 ml ethyl ether. The mixture was agitated for 5 minutes, followed by addition of 0.007 mol of amine. The reaction mixture was agitated at ambient temperature for 2 hours. The resulting precipitate was dried on suction pump, washed several times in water, dried and recrystallised.

EXAMPLE 19

2-(2-aminoethyl morpholino)-2-benzamidoindan-1,3-dione

Raw materials: 2-benzamido-2-chloroindan-1,3-dione 4-(2-aminoethyl)-morpholine

Yield: 85%; M.P.: 158° C.; IR: ν NH=3120 cm$^{-1}$, ν CO=1760, 1720 and 1630 cm$^{-1}$.

Recrystallisation solvent: ethyl ether

EXAMPLE 20

2-benzamido-2-[1-(2-pyridyl)-piperazino]indan-1,3-dione

Raw materials: 2-benzamido-2-chloroindan-1,3-dione 1-(2-pyridyl)-piperazine

Yield: 70%; M.P.: 186° C.; IR: ν NH=3300 cm$^{-1}$, ν CO=1750 and 1720 cm$^{-1}$.

Recrystallisation solvent: ethyl ether

EXAMPLE 21

2-benzamido-2-[1-(4-fluorophenyl)-piperazino] indan-1,3-dione

Raw materials: 2-benzamido-2-chloroindan-1,3-dione 1-(4-fluorophenyl)-piperazine Yield: 65%; M.P.: 162° C.; IR: ν NH=3200 cm$^{-1}$, ν CO=1750, 1720 and 1630 cm$^{-1}$.

Recrystallisation solvent: ethyl ether

D/ Preparation of compounds having the formulae (Ih) and (Ii)

Method ⑤

Five drops of concentrated hydrochloric acid (10N) was added to a suspension of 0.008 mol of compound (Ia) or (Ib) in 100 ml ethanol. The reaction mixture was refluxed for 30 minutes. The resulting yellow precipitate was dried on suction pump when cold, dried and recrystallised.

Method ⑥

0.01 mol of the corresponding hydrazide in solution in 50 ml ethanol and five drops of concentrated hydrochloric acid (10N) were added to a solution of 0.01 mol ninhydrin in 50 ml ethanol.

The reaction mixture was refluxed for 30 minutes and cooled to about 50° C. and the resulting yellow precipitate was dried on suction pump, dried and recrystallised.

Method ⑦

A suspension of 1.5 g of compound (Ia) or (Ib) in 100 ml acetonitrile was refluxed for 30 minutes. The resulting solution was refluxed for a further 30 minutes until a yellow precipitate was obtained, which was dried after cooling.

Method ⑧

0.01 mol of hydrazide was added to a solution of 0.01 mol ninhydrine in 60 ml ethanol. The reaction mixture was refluxed for 2 hours. The resulting orange precipitate was dried on suction pump, dried and recrystallised.

EXAMPLE 22

2-methoxycarbonyl hydrazonoindan-1,3-dione
Method ⑤

Raw material: 2-hydroxy-2-methoxycarbonyl hydrazinoindan-1,3-dione

Yield: 80%; M.P.: 206° C.; IR: ν NH=3220 cm$^{-1}$, ν CO=1775, 1720 and 1680 cm$^{-1}$.

Recrystallisation solvent: acetonitrile

EXAMPLE 23

2-methoxycarbonyl hydrazono-5-methoxyindan-1,3-dione

Method ⑤

Raw material: 2-hydroxy-2-methoxycarbonyl hydrazino-5-methoxyindan-1,3-dione

Yield: 81%; M.P.: 190° C.; IR: ν NH=3270 cm$^{-1}$, ν CO=1760 and 1720 cm$^{-1}$.

Recrystallisation solvent: ethyl acetate

EXAMPLE 24

2-benzoyl hydrazonoindan-1,3-dione

Method ⑤

Raw material: 2-benzoylhydrazino-2-hydroxyindan-1,3-dione

EXAMPLE 25

2-benzoyl hydrazono-5-methoxyindan-1,3-dione

Method ⑤

Raw material: 2-benzoyl hydrazino-2-hydroxy-5-methoxyindan-1,3-dione

Yield: 98%; M.P.: 218° C.; IR: ν NH=3250 cm$^{-1}$, ν CO=1735 and 1680 cm$^{-1}$.

Recrystallisation solvent: ethyl acetate

EXAMPLE 26

2-(2-methylbenzoylhydrazono)-indan-1,3-dione

Method ⑤

Raw material: 2-hydroxy-2-(2-methyl benzoylhydrazino)-indan-1,3-dione

Yield: 98%; M.P.: 232° C.; IR: ν NH=3230 cm$^{-1}$, ν CO=1720 and 1675 cm$^{-1}$.

Recrystallisation solvent: methanol

EXAMPLE 27

2-(3-methylbenzoylhydrazono)-indan-1,3-dione

Method ⑥

Raw materials: indan-1,2,3-trione monohydrate 3-methyl benzoylhydrazine

Yield: 95%; M.P.: 192° C.; IR: ν NH=3230 cm$^{-1}$, ν CO=1720 and 1675 cm$^{-1}$.

Recrystallisation solvent: ethyl acetate

EXAMPLE 28

2-(4-methyl benzoylhydrazono)-indan-1,3-dione

Method ⑥

Raw materials: Indan-1,2,3-trione monohydrate 4-methyl benzoylhydrazine

Yield: 95%; M.P.: 196° C.; IR: ν NH=3230 cm$^{-1}$, ν CO=1720 and 1675 cm$^{-1}$.

Recrystallisation solvent: ethanol

EXAMPLE 29

2-(2-hydroxybenzoylhydrazono)-indan-1,3-dione

Method ⑤

Raw material: 2-hydroxy-2-(2-hydroxybenzoyl hydrazino)-indan-1,3-dione

Yield: 98%; M.P.: 190° C.; IR: ν OH=3380 cm$^{-1}$, ν NH=3140 cm$^{-1}$, ν CO=1730, 1690 and 1655 cm$^{-1}$.

Recrystallisation solvent: ethyl acetate

EXAMPLE 30

2-(3-hydroxybenzoylhydrazono)-indan-1,3-dione

Method ⑤

Raw material: 2-hydroxy-2-(3-hydroxybenzoylhydrazino)-indan-1,3-dione

Yield: 92%; M.P.: 202° C.; IR: ν NH=3250 cm$^{-1}$, ν CO=1730, and 1680 cm$^{-1}$.

Recrystallisation solvent: acetonitrile

EXAMPLE 31

2-(4-hydroxybenzoylhydrazono)-indan-1,3-dione

Method ⑥

Raw materials: indan-1,2,3-trione monohydrate 4-hydroxybenzoyl hydrazine

Yield: 90%; M.P.: >265° C.; IR: ν OH/NH=3330 cm$^{-1}$, ν CO=1730 and 1680 cm$^{-1}$.

Recrystallisation solvent: acetonitrile

EXAMPLE 32

2-(3,4-dihydroxybenzoylhydrazono)-indan-1,3-dione

Method ⑥

Raw materials: Indan-1,2,3-trione monohydrate 3,4-dihydroxybenzohydrazine hydrochloride Yield: 70%; M.P.: >260° C.; IR: ν OH=3320 cm$^{-1}$, ν NH=3250 cm$^{-1}$, ν CO=1730 and 1675 cm$^{-1}$.

Recrystallisation solvent: ethanol

EXAMPLE 33

2-(5-phenyl-2-(N-pyrrolyl)thiophen-3-carbonyl hydrazono)-indan-1,3-dione

Method ⑤

Raw material: 2-hydoxy-2-(5-phenyl-2-(N-pyrrolyl)-thiophen-3-carbonyl hydrazino)-indan-1,3-dione Yield: 83%; M.P.: 198° C.; IR: ν NH=3230 cm$^{-1}$, ν CO=1715 and 1660 cm$^{-1}$.

Recrystallisation solvent: ethyl acetate

EXAMPLE 34

2-oxamoyl hydrazonoindan-1,3-dione

Method ⑤

Raw material: 2-hydroxy-2-oxamoyl hydrazinoindan-1,3-dione

Yield: 70%; M P.: >265° C.; IR: ν OH=3440 cm$^{-1}$, ν NH=3310 cm$^{-1}$, ν CO=1720, 1700 and 1670 cm$^{-1}$.

Recrystallisation solvent: ethyl acetate

EXAMPLE 35

3-(3-hydroxybenzoylhydrazono)-5-methoxyindan-1,3-dione

Method ⑥

Raw materials: 5-methoxyindan-1,2,3-trione monohydrate 3-hydroxybenzoyl hydrazine Yield: 70%; M.P.: 236° C.; IR: ν OH/NH=3400 cm$^{-1}$, ν CO=1745 and 1680 cm$^{-1}$ Recrystallisation solvent: ethyl acetate

EXAMPLE 36

2-(3,4-dimethoxybenzoyl hydrazono)-indan-1,3-dione

Method ⑤

Raw material: 2-hydroxy-2-(3,4-dimethoxybenzoyl hydrazino)-indan-1,3-dione

Yield: 60%; M.P.>265° C.; IR: ν NH=3250 cm⁻¹, ν CO=1730 and 1680 cm⁻¹

Recrystallisation solvent: ethyl acetate

EXAMPLE 37

2-(2-hydroxy-3-methylbenzoyl hydrazono)-indan-1,3-dione

Method ⑤

Raw material: 2-hydroxy-2-(2-hydroxy-3-methylbenzoyl hydrazino)-indan-1,3-dione

Yield: 75%; M.P.>265° C.; IR: ν NH=3250 cm⁻¹, ν CO=1730 and 1680 cm⁻¹

Precipitate washed in water

EXAMPLE 38

2-(4-hydroxy-3-methoxybenzoyl hydrazono)-indan-1,3-dione

Method ⑥

Raw materials: Indan-1,2,3-trione monohydrate 4-hydroxy-3-methoxybenzoyl hydrazine Yield: 70%; M.P. 264° C.; IR: ν OH=3330 cm⁻¹, ν NH=3250 cm⁻¹, ν CO=1730 and 1675 cm⁻¹

Recrystallisation solvent: dioxan

EXAMPLE 39

2-(2-thenoyl hydrazono)-indan-1,3-dione

Method ⑧

Raw materials: Indan-1,2,3-trione monohydrate 2-thenoyl hydrazine

Yield: 80%; M.P. 182° C.; IR: ν NH=3200 cm⁻¹, ν CO=1720 and 1670 cm⁻¹

Recrystallisation solvent: ethanol

EXAMPLE 40

2-(2-furoyl hydrazono)-indan-1,3-dione

Raw materials: Indan-1,2,3-trione monohydrate 2-furoyl hydrazine

Yield: 70%; M.P. 222° C.; IR: ν NH=3200 cm⁻¹, ν CO=1720 and 1670 cm⁻¹

Recrystallisation solvent: ethanol

EXAMPLE 41

2-(4-aminobenzoyl hydrazono)-indan-1,3-dione

Method ⑤ and ⑥

Raw materials: Indan-1,2,3-trione monohydrate 4-aminobenzohydrazine hydrochloride Yield: 80%; M.P.>260° C.; IR: ν NH=3340 and 3220 cm⁻¹, ν CO=1730 and 1680 cm⁻¹

Recrystallisation solvent: acetonitrile

EXAMPLE 42

2-(4-trifluoroacetyl aminobenzoyl hydrazono)-indan-1,3-dione 1 g (0.003 mol) of 2-(4-aminobenzoyl hydrazono)-indan-1,3-dione was added to a mixture of 8 ml trifluoroacetic anhydride and 8 ml trifluoroacetic acid. The reaction mixture was refluxed for 10 minutes and the yellow precipitate obtained after cooling was washed several times in water, dried on suction pump, dried and recrystallised.

Yield: 75%; M.P.>260° C.; IR: ν NH=3220 cm⁻¹, ν CO=1740 and 1690 cm⁻¹.

Recrystallisation solvent: ethyl acetate

EXAMPLE 43

2-(4-acetyl aminobenzoyl hydrazono)-indan-1,3-dione 1 g (0.003 mol) of 2-(4-aminobenzoyl hydrazono)-indan-1,3-dione was added to a mixture of 8 ml acetic anhydride and 8 ml acetic acid. The reaction mixture was agitated at ambient temperature for 30 minutes and the yellow precipitate obtained after cooling was washed several times in water, dried on suction pump, dried and recrystallised.

Yield: 60%; M.P.>260° C.; IR: ν NH=3220 cm⁻¹, ν CO=1740 and 1690 cm⁻¹

Recrystallisation solvent: ethyl acetate

EXAMPLE 44

2-[(2-pyrazinyl)carbonyl hydrazono]-indan-1,3-dione

Method ⑥

Raw materials: indan-1,2,3-trione monohydrate 2-hydrazinocarbonyl pyrazine

Yield: 95%; M.P. 278° C.; IR (KBr): ν NH=3230 cm⁻¹, ν C=O=1720 and 1700 cm⁻¹

NMR of ¹H (200 MHz, DMSO d₆); δ (ppm) 14.38 (1s, 1H, NH); 9.40 (s, 1H, H-3'); 9.04 and 8.92 (2dd, 2H, H-5', H-6', J5'–6'=4 Hz); 8.03 (s, 4H, H-4, H-5, H-6, H-7)

Recrystallisation solvent: dichloromethane

EXAMPLE 45

2-[(3-furyl)carbonyl hydrazono]-indan-1,3-dione

Method ⑥

Raw materials: Indan-1,2,3-trione monohydrate 3-hydrazinocarbonyl furan

Yield: 59%; M.P. 180° C.; IR (KBr): ν NH=3400 cm⁻¹, ν C=O=1760 and 1690 cm⁻¹

NMR of ¹H (200 MHz, DMSO d₆): δ (ppm) 12.70 (1s, 1H, NH); 8.59 (s, 1H, H-2'); 8.02 (s, 4H, H-4, H5, H-6, H-7); 7.91 (s, 1H, H-5'); 6.98 (s, 1H, H-4')

Recrystallisation solvent: acetone

EXAMPLE 46

2-[(2-pyrrolyl)carbonylhydrazono]-indan-1,3-dione

Method ⑥

Raw materials: Indan-1,2,3-trione monohydrate 2-hydrazinocarbonyl pyrrole

Yield: 75%; M.P. 235° C.; IR (KBr): ν NH=3250 and 3125 cm⁻¹, ν C=O=1775 and 1700 cm⁻¹

NMR ¹H (200 MHz, DMSO d₆): δ (ppm) 13.21 (1s, 1H, NHCO); 12.25 (1s, 1H, NH); 8.00 (s, 4H, H-4, H-5, H-6, H-7); 7.22 (m, 1H, H-5'); 7.03 (m, 1H, H-3'); 6.33 (m, 1H, H-4')

Recrystallisation solvent: ethyl acetate

EXAMPLE 47

2-[(3-pyrrolyl)carbonyl hydrazono]-indan-1,3-dione

Method (6)

Raw materials: Indan-1,2,3-trione monohydrate 3-hydrazinocarbonyl pyrrole

Yield: 60%; M.P. 240° C.; IR (KBr): ν NH=3250 and 3125 cm$^{-1}$; ν C=O=1775 and 1700 cm$^{-1}$ NMR $^1$H (200 MHz, DMSO d$_6$): δ (ppm) 13.28 (1s, 1H, NHCO); 12.00 (1s, 1H, NH); 7.95 (s, 4H, H-4, H-5, H-6, H-7); 7.10 (m, 1H, H-2'); 7.00 (m, 1H, H-5'); 6.25 (m, 1H, H-4').

Recrystallisation solvent: ethyl acetate

EXAMPLE 48

2-[(3-thienyl)carbonyl hydrazono]-indan-1,3-dione

Method (6)

Raw materials: Indan-1,2,3-trione monohydrate 3-hydrazinocarbonyl thiophen

Yield: 75%; M.P. 178° C.; IR (KBr): ν NH=3050 cm$^{-1}$, ν C=O=1730, 1690 and 1680 cm$^{-1}$ NMR $^1$H (200 MHz, DMSO d$_6$): δ (ppm) 13.28 (1s, 1H, NH); 7.51 (s, 1H, H-2'); 8.02 (s, 4H, H-4, H-5, H-6, H-7); 7.80 (d, 1H, H-5', J4'-5'=5 Hz); 7.61 (d, 1H, H-4', J4'-5'=5 Hz)

Recrystallisation solvent: ethyl acetate

EXAMPLE 49

2-[(4-fluorophenyl)carbonyl hydrazono]-indan-1,3-dione

Method (6)

Raw materials: Indan-1,2,3 trione monohydrate 4-fluoro-hydrazinocarbonyl benzene Yield: 71%; M.P.>260° C.; IR (KBr): ν NH=3120 cm$^{-1}$, ν C=O=1730 and 1665 cm$^{-1}$ NMR of $^1$H (200 MHz, DMSO d$_6$): δ (ppm) 13.55 (1s, 1H, NH); 8.05 (1s, 6H, H-4, H-5, H-6, H-7, H-3', H-5'); 7.55 (t, 2H, H-2', H-6', J2'-3' and J5'-6'=6.6 Hz)

Recrystallisation solvent: ethyl acetate

E/ Preparation of compounds having the formulae (Ij) and (Ik)

Method (9)

0.01 of the corresponding hydrazine hydrochloride in solution in 15 ml water was added to a solution of 0.01 mol ninhydrin in 60 ml ethanol.

The reaction mixture was refluxed for 30 minutes. The precipitate formed was dried on suction pump when hot, dried and recrystallised.

EXAMPLE 50

2-(2,4-dichlorophenyl hydrazono)-indan-1,3-dione

Raw materials: Indan-1,2,3-trione monohydrate 2,4-dichlorophenyl hydrazine

Yield: 70%; M.P.: 238° C.; IR: ν NH=3200 cm$^{-1}$, ν CO=1720 and 1670 cm$^{-1}$ Recrystallisation solvent: ethyl acetate

EXAMPLE 51

2-(3-chloro-4-methylphenyl hydrazono)-indan-1,3-dione

Raw materials: Indan-1,2,3-trione monohydrate 3-chloro-4-methylphenyl hydrazine hydrochloride Yield: 70%; M.P.: 234° C.; IR: ν NH=3140 cm$^{-1}$, ν CO=1710 and 1660 cm$^{-1}$ Recrystallisation solvent: ethyl acetate

EXAMPLE 52

2-(4-methylsulphonylphenylhydrazono)-indan-1,3-dione

Raw materials: Indan-1,2,3-trione monohydrate 4-methylsulphonylphenylhydrazine hydrochloride Yield: 90%; M.P.>265° C.; IR: ν NH=3200 cm$^{-1}$, ν CO=1720 and 1670 cm$^{-1}$ Precipitate washed in ethyl acetate

EXAMPLE 53

5-hydroxy-2-(4-methylsulphonylphenylhydrazono)-indan-1,3-dione

Raw materials: 5-hydroxyindan-1,2,3-trione monohydrate 4-methylsulphonylphenylhydrazine hydrochloride Yield: 90%; M.P.: >265° C.; IR: ν NH/OH=3320 cm$^{-1}$, ν CO=1710 and 1670 cm$^{-1}$ Precipitate washed in ethyl acetate

EXAMPLE 54

2-(4-N-methylmethanesulphonamidophenylhydrazono)-indan-1,3-dione

Raw materials: Indan-1,2,3-trione monohydrate 4-(N-methyl methanesulphonamido)-phenyl hydrazine hydrochloride Yield: 90%; M.P.: >265° C.; IR: ν NH=3300 cm$^{-1}$, ν CO=1720 and 1675 cm$^{-1}$ Precipitate washed in ethyl acetate

EXAMPLE 55

5-methoxy-2-(4-N-methylmethanesulphonamidophenyl-hydrazono)-indan-1,3-dione

Raw materials: 5-methoxyindan-1,2,3-trione monohydrate 4-(N-methylmethanesulphonamido)phenylhydrazine hydrochloride Yield: 90%; M.P.: 236° C.; IR: ν NH=3280 cm$^{-1}$, ν CO=1715 and 1670 cm$^{-1}$ Precipitate washed in ethyl acetate

EXAMPLE 56

2-(2-hydroxyphenyl)-iminoindan-1,3-dione 0.01 mol of 2-hydroxyaniline was added to a solution of 0.01 mol ninhydrin in 200 ml ethanol. The reaction mixture was refluxed for an hour. The resulting precipitate was dried on suction pump, washed in ethyl ether and recrystallised from acetonitrile.

Method (10)

Yield: 70%; M.P. 265° C.; IR: ν OH=3500 cm$^{-1}$, ν CO=1750 cm$^{-1}$

F/ Preparation of formula (II) compounds

Method (11)

34 mmols of isobutyl chloroformate and 34 mmols of N-methyl morpholine were added to 34 mmols of aryl carboxylic acid in solution in 68 ml ethyl acetate, followed dropwise at −10° C. by 34 mmols of 2-hydroxyimino-indan-1,3-dione in solution in 25 ml DMF. After one hour at −10° C., 15 hours at ambient temperature and 5 hours at 40° C., the precipitate formed was eliminated by filtration on fritted glass and washed in ethyl acetate. The filtrate was then washed with a saturated solution of sodium hydrogen carbonate dried on magnesium sulphate and evaporated at reduced pressure. The resulting yellow crystals were recrystallised then dried overnight in vacuo at 50° C.

EXAMPLE 57

2-phenylcarbonyloxyimino-indan-1,3-dione

Raw materials: 2-hydroxyimino-indan-1,3-dione benzene carboxylic acid

Yield: 68%; M.P.: 178° C.; IR (KBr): ν C=O=1780 and 1700 cm$^{-1}$

NMR $^1$H (200 MHz, DMSO, d$_6$): δ (ppm) 8.23 (m, 2H, H-2', H-6', J2'–3' and 5'–6'=8.4 Hz); 8.05 (s, 4H, H-4, H-5, H-6, H-7); 7.78 (m, 1H, H-4'); 7.70 (m, 2H, H-3', H-5')

Recrystallisation solvent: chloroform/petroleum ether 50/50%

EXAMPLE 58

2-(4-fluorophenyl)carbonyloxyimino-indan-1,3-dione

Raw materials: 2-hydroxyimino-indan-1,3-dione 4-fluoro-benzene carboxylic acid

Yield: 75%; M.P.: 198° C.; IR (KBr): ν CO=1765 and 1700 cm$^{-1}$

NMR $^1$H (200 MHz, DMSO d$_6$): δ (ppm) 8.30 (m, 2H, H-3', H-5'); 8.05 (s, 4H, H-4, H-5, H-6, H-7); 7.53 (t, 2H, H-2', H-6', J2'–3' and 5'–6'=8.9 Hz)

Recrystallisation solvent: chloroform/petroleum ether (50/50)

G/ Preparation of formula (Im) compounds
Method (12)

10 mmols of aryl aminocarbonyl hydrazine in solution in 60 ml ethanol were added to a solution of 10 mmols of 2-acetyl-indan-1,3-dione in 30 ml ethanol.

The reaction mixture was refluxed for 30 minutes and the resulting white precipitate was dried on suction pump when hot, dried and recrystallised.

EXAMPLE 59

3-[methyl(phenylaminocarbonylhydrazino) methylene]-indan-1,3-dione

Raw materials: 2-acetyl-indan-1,3-dione phenyl aminocarbonyl hydrazine

Yield: 71%; M.P.: 213° C.; IR (KBr): ν NH=3280 and 3250 cm$^{-1}$, ν C=O=1700, 1660 and 1600 cm$^{-1}$ NMR $^1$H (200 MHz, DMSO d$_6$): δ (ppm) 11.55 (s, 1H, NH); 9.26 (s, 1H, NH); 8.84 (s, 1H, NH); 7.60 (s, 4H, H-4, H-5, H-6, H-7); 7.41 (d, 2H, H-2', H-6', JH3'–2'=JH6'–5'=8.41 Hz); 7.22 (t, 2H, H-3', H-5', JH3'–2'=JH6'–5'=8.41 Hz, JH3'–4'=6.92 Hz); 6.93 (t, 1H, H-4', JH3'–4'=6.92 Hz); 2.51 (s, 3H, CH$_3$)

Recrystallisation solvent: acetone

EXAMPLE 60

2-[(4-fluorophenyl)aminocarbonyl hydrazinomethyl methylene]-indan-1,3-dione

Raw materials: 2-acetyl-indan-1,3-dione (4-fluorophenyl) aminocarbonyl hydrazine Yield: 98%; M.P.: 213° C.; IR (KBr): ν NH=3260 and 3240 cm$^{-1}$, ν CO=1700, 1660 and 1600 cm$^{-1}$ NMR $^1$H (200 MHz, DMSO, d$_6$): δ (ppm) 11.68 (s, 1H, NH); 9.44 (s, 1H, NH); 9.00 (s, 1H, NH); 7.75 (s, 4H, H-4, H-5, H-6, H-7); 7.57 (m, 2H, H-3', H-5'); 7.22 (t, 2H, H-2', H-6', JH2'–3' and 5'–6'=8.9 Hz); 2.66 (s, CH$_3$)

Recrystallisation solvent: acetone

EXAMPLE 61

2-[(4-hydroxyphenyl)carbonyl hydrazinomethyl methylene]-indan-1,3-dione

Raw materials: 2-acetyl-indan-1,3-dione (4-hydroxyphenyl)carbonyl hydrazine

Yield: 88%; M.P.: 257° C.; IR (KBr): ν NH, OH=3210 cm$^{-1}$, ν C=O=1700, 1640 and 1600 cm$^{-1}$ NMR of $^1$H (200 MHz, DMSO d$_6$ ): δ (ppm) 11.98 (s, 1H, NH); 11.16 (s, 1H, NH); 10.40 (s, 1H, OH); 7.94 (d, 2H, H-3', H-5', JH2'–3' and 5'–6'=8.41 Hz); 7.78 (s, 4H, H-4, H-5, H-6, H-7); 7.00 (d, 2H, H-2', H-6', JH2'–3' and 5'–6'= 8.41 Hz); 2.73 (s, 3H, CH$_3$)

Recrystallisation solvent: acetone

H/ Preparation of formula (In) compounds

EXAMPLE 62

2-oximino-1-(4-phenyl semicarbazono)-3-indanone 0.01 mol of 4-phenyl semicarbazide hydrochloride in solution in 10 ml water was added to a solution of 0.01 mol of 2-oximino indan-1,3-dione in 60 ml ethanol. The reaction mixture was refluxed for 1 hour. The precipitate formed was centrifuged when hot, dried and recrystallised from acetonitrile.

Method (13)

Yield: 60%; M.P: >265° C.; IR: ν OH=3340 cm$^{-1}$, ν NH=3250 cm$^{-1}$, ν CO=1700 and 1680 cm$^{-1}$.

Note that the above infra-red spectra were determined with KBr pellets.

The following are the NMR spectra of some compounds according to the invention.

These spectra were taken on an NMR 200 MHz apparatus, the compounds being in solution in DMSO (D6). The spectra, like those given hereinabove, are described in accordance with the following protocol: shift (δ) in ppm, shape of signal, number of protons, nature of protons, coupling constants if any.

The aromatic protons on indan are numbered as follows:

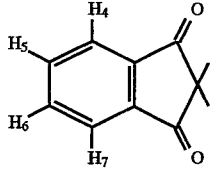

In the case where R and R$_1$ comprise a heterocyclic ring or form a group containing a heterocyclic ring, the protons in the ring are numbered from the heteroatom in the direction of the bond to the main substrate.

NMR spectra

Example a

5-Hydroxyindane-1,3-dione 7.78 (d, 1H, H-7, J H6–7=8.3 Hz)
7.26 (d, 1H, H-6, J H6–7=8.3 Hz)

7.11 (1s, 1H, H-4)
3.25 (s, 3H, CH2)

Example b

2-Bromo-5-hydroxindane-1,3-dione 11.55 (1s, OH)
7.90 (dd, 1H, H-6, J H6–4=2.93 Hz; J H6–7=8.3 Hz)
7.39 (d, 1H, H-7, J H6–7=8.3 Hz)
7.21 (s, 1H, H-4)
5.50 (s, 1H, H2)

Example c

5-Hydroxyindane-1,2,3-trione, monohydrate 1.50 (1s, 1H, OH)
7.90 (d, 1H, H7, J H6–7=5.9 Hz)
7.40 (m, 2H, H4, H6)

Example d 5,6-Dimethoxyindane-1,2,3-trione, monohydrate 7.40 (1s, 2H, H-4, H-7)
4.03 (s, 6H, 2CH3O)

Example e

6-Hydroxy-6-methoxyindane-1,2,3-trione, monohydrate 11.21 (1s, 1H, OH)
7.28 (m, 2H, H-4, H-7) 4.03 (s, 6H, 2CH$_3$O)

Example f 2-oximino-5-hydroxyindane-1,3-dione 9.16 (1s, 1H, OH)
7.83 (dd, 1H, H6, JH6–7=9.0 Hz & JH4–6=3.0 Hz)
7.21 (m, 2H, H7, H4)

Example 1

2-Hydroxy-2-methoxycarbonylhydrazinoindane-1,3-dione 8.22 (1s, 1H, NH)
8.01 (s, 4H, H-4, H-5, H-6, H-7)
6.77 (1s, 1H, NH)
5.86 (s, 1H, OH)
3.46 (s, 3H, CH3)

Example 2

2-Hydroxy-2-methoxycarbonylhydrazino-5-methoxyindane-1,3-dione 8.43 (1s, 1H, NH)
7.94 (dd, 1H, H-7, J H4–7=1.5 Hz, J H6–7=8.3 Hz)
7.53 (dd, 1H, H-6, J H4–6=1.5 Hz, J H6–7=8.3 Hz)
7.39 (s, 1H, H-4)
6.78 (s, 1H, OH)
5.75 (1s, 1H, NH)
3.97 (s, 3H, CH3O)
3.47 (s, 3H, CH3OCO)

Example 3

2-Benzoylhydrazino-2-hydroxy-indane-1,3-dione 9.97 (1s, 1H, NH)
8.01 (s, 4H, H-4, H-5, H-6, H-7)
7.74 et 7.49 (2 m, 5H, Ph)
7.32 (1s, 1H, OH)
6.33 (s, 1H, NH)

Example 4

2-Benzoylhydrazino-2-hydroxy-5-methoxyindane-1,3-dione 9.91 (d, 1H, NH, J NH—NH=3.9 Hz)
7.91 (d, 1H, H-7, J H 6–7=8.3 Hz)
7.75 (d, 1H, H-6, J H 6–7=8.3 Hz)
7.50 (m, 6H, H-4& Ph)
7.09 (s, 1H, OH)
6.23 (d, 1H, NH, J NH—NH=3.9 Hz)
3.97 (s, 3H, CH3O)

2-Hydroxy-2-(2-methoxybenzoylhydrazino)-indane-1,3-dione 9.59 (d, 1H, NH, J NH—NH=2.9 Hz)
8.03 (s, 4H, H-4, H-5, H-6, H-7)
7.74 (d, 1H, H-6', J H 5'–6'=7.8 Hz)
7.50 (t, 1H, H-5', J H 5'–6' & 4'–5'=7.8 Hz,)
7.15 (s ,1H, OH)
7.05 (m, 2H H-3', H-5')
6.36 (d, 1H, NH, J NH—NH=2.9 Hz)
3.91 (s, 3H, CH3O)

2-Hydroxy-2-(3-methoxybenzoylhydrazino)-indane-1,3-dione 9.97 (1s, 1H, NH)
7.99 (s, 4H, H-4, H-5, H-6, H-7)
7.33 (m, 3H, H-2', H-3', H-4')
7.11 (1s, 2H, H-6', OH)
6.33 (1s, 1H, NH)
3.77 (s, 3H, OCH3)

2-Hydroxy-2-(3-methoxybenzoylhydrazino)-5-methoxy indane-1,3-dione 9.91 (1s, 1H, NH)
7.93 (d, 1H, H-7, J H6–7=8.3 Hz)
7.53 (d, 1H, H-6, J H6–7=8.3 Hz)
7.35 (m, 5H, H-4 & Ph)
7.10 (s ,1H, OH)
6.22 (1s, 1H, NH)
3.97 (s, 3H, CH3O)
3.78 (s, 31H, CH3O, Ph)

2-Hydroxy-2-(4-methoxybenzoylhydrazino)-indane-1,3-dione 9.83 (1s, 1H, NH,)
7.75 (d, 2H, H-2', H-6', J H5'–6' & 2'–3'=8.3 Hz)
8.00 (s, 4H, H-4, H-5, H-6, H-7)
7.17 (s, 1H, OH)
6.98 (d, 2H, H-3', H-5', J H5'–6' & 2'–3'=8.3 Hz)
6.29 (1s, 1H, NH)
3.80 (s, 3H, CH3O)

Example 6

2-Hydroxy-2-(2-methylbenzoylhydrazino)-indane-1,3-dione 9.69 (d, 1H, NH, J NH—NH=3.9 Hz)
8.01 (s, 4H, H-4, H-5, H-6, H-7)
7.25 (m, 4H, H-3',H-4', H-5', H-6')
7.06 (s, 1H, OH)

6.32 (d, 1H, NH, J NH—NH=3.9 Hz)
2.26 (s, 3H, CH3)

Example 7

2-Hydroxy-2-(3-methylbenzoylhydrazino)-indane-1,3-dione 9.90 (1s, 1H, NH)
8.00 (s, 4H, H-4, H-5, H-6, H-7)
7.55 & 7.30 (2m, 4H, H-2',H-4', H-5', H-6')
7.08 (s, 1H, OH)
6.30 (1s, 1H, NH)
2.35 (s, 3H, CH3)

Example 8

2-Hydroxy-2-(4-methylbenzoylhydrazino)-indane-1,3-dione 9.89 (d, 1H, NH, J NH—NH=3.9 Hz)
8.00 (s, 4H, H-4, H-5, H-6, H-7)
7.66 (d, 21–1, H-2', H-6', J H2' & 5'–6'=8.3 Hz)
7.25 (d, 2H, H3', H-5', J H2'–3' & 5'–6'=3.3 Hz)
7.12 (s, 1H, OH)
6.30 (d, 1H, NH, J NH—NH=3.9 Hz)
2.35 (s, 3H, CH3)

Example 9

2-Hydroxy-2-(2-hydroxybenzoylhydrazino)-indane-1,3-dione 1.70 (s, 1H, PhO$\underline{H}$)
10.07 (1s, 1H, NH)
8.00 (s, 4H, H-4, H-5, H-6, H-7)
7.84 (d, 1H, H-6', J H5'–6'=7.8 Hz)
7.40 (m, 1H, H-5')
7.05 (s, 1H, OH)
6.90 (m, 2H, H-3', H-4')
6.35 (1s, 1H, NH)

Example 10

2-Hydroxy-2-(3-hydroxybenzoylhydrazino)-indane-1,3-dione 9.83 (d, 1H, NH, J NH—NH=3.9 Hz)
9.70 (s, 1H, PhO$\underline{H}$)
8.00 (s, 4H, H-4, H-5, H-6, H-7)
7.15 (m, 5H, H-2',H-4', H-5', H-6', OH)
6.30 (d, 1H, NH, J NH—NH=3.9 Hz)

Example 11

2-(3,4-Dimethoxybenzoylhydrazino)-2-hydroxyindane-1,3-dione 9.85 (1s, 1H, NH)
8.00 (s, 4H, H-4, H-5, H-6, H-7)
7.35 (m, 4H, H-2', H-5', H-6', OH)
6.30 (1s, 1H, NH)
3.78 et 3.79 (2 s, 6H, CH3O)

Example 12

2-Hydroxy-2-(2-hydroxy-3-methylbenzoylhydrazino) indane-1,3-dione 12.39 (s, 1H, PhOH)
10.31 (1s, 1H, NH)
8.02 (s, 4H, H-4, H-5, H-6, H-7)
7.74 (d, 1H, H-6', J H5'–6'=7.8 Hz)
7.30 (d, 1H, H-4', J H4'–5'=7.8 Hz)
6.97 (d, 1H, OH)
6.79 (t, 1H, H-5', J H5'–6' & 4'–5'=7.8 Hz)
6.41 (1s, 1H, NH)
2.15 (s, 3H, CH3)

Example 13

2-Hydroxy-2-(4-hydroxy-3-methoxybenzoylhydrazino)indane-1,3-dione 9.9 (1s, 1H, NH)
9.82 (s, 1H, PhOH)
8.00 (s, 4H, H-4, H-5, H-6, H-7)
7.38 (m, 3H, H-2', H-6', OH)
6.80 (d, 1H, H-5', J H5'–6'=8.3 Hz)
6.34 (1s, 1H, NH)
3.81 (s, 3H, CH3O)

Example 14

2-Hydroxy-2-(5-phenyl-2-(N-pyrrolyl)thiophen-3-carbonylhydrazino)-indane-1,3-dione 10.05 (s, 1H, OH)
9.9 (1s, 1H, NH)
8.00 (s, 4H, H-4, H-5, H-6, H-7)
7.66 et 7.38 (m, 7H, 2H pyrrole, 5H phenyl)
7.05 (s, 3H, OH, 2H pyrrole)
6.36 (1s, 1H, NH)
6.25 (s, 1H, thiophen)

2-Hydroxy-2-nicotinoylhydrazino-indane-1,3-dione 10.23 (1s, 1H, NH)
8.94 (s, 1H, H-2')
8.75 (m, 1H, H-6')
8.73 (m, 1H, H-4')
8.05 (s, 4H, H-4, H-5, H-6, H-7)
7.54 (m, 1H, H-5')
7.09 (s, 1H, OH)
6.43 (1s, 1H, NH)

2-Hydroxy-2-isonicotinoylhydrazino-indane-1,3-dione 10.27 (1s, 1H, NH)
8.02 (m, 2H, H-2', H-6')
8.02 (s, 4H, H-4, H-5, H-6, H-7)
7.69 (m, 2H, H-3', H-5')
7.04 (s, 1H, OH)
6.42 (1s, 1H, NH)

Example 15

2-Hydroxy-2-oxamoylhydrazino-indane-1,3-dione 9.53 (1s, 1H, NH)
8.11 (s, 1H, NH)
8.02 (s, 4H, H-4, H-5, H-6, H-7)
7.86 (s, 1H, OH)
7.17 (s, 1H, OH)
6.20 (1s, 1H, NH)

2-Hydroxy-2-isonicotinoylhydrazino-5-methoxy-indane-1,3-dione 10.22 (d, 1H, NH, J NH—NH=3.9 Hz)
8.73 (d, 2H, H-3', H-5', J H2'–3' & 5'–6'=5.8 Hz)

7.94 (d, 1H, H-7, J H6–7=8.8 Hz)
7.69 (d,2H, H-2', H-6', J H2'–3' & 5'–6'=5.8 Hz)
7.45 (dd, 1H, H-6,J H4–6=2.4 & 6–7=8.8 Hz)
7.41 (d, 1H, H-4, J H4–6=2.4 Hz)
7.04 (s, 1H, OH)
6.30 (d, 1H, NH, J NH—NH=3.9 Hz)
3.38 (s,3H, CH3)

Example 16

2-Hydroxy-2-(indole-3-acetylhydrazino)-indane-1,3-dione 10.84 (s, 1H, NH)
9.52 (d, 1H, NH, J NH—NH=3.9 Hz)
7.95 (s, 4H, H-4, H-5, H-6, H-7)
7.50 (d, 1H, H-4', J H4'–5'=7.8 Hz)
7.30 (d, 1H, H-5', J H4'–5'=7.8 Hz)
7.14 (s, 1H, OH)
6.94a 7.04 (m, 3H, H-2', H-6', H-7') 6.10 (d, 1H, NH, J NH—NH=3.9 Hz) 3.45 (s, 2H, CH2)

2-Benzamido-2-hydroxyindane-1,3-dione 9.85 (s, 1H, NH)
8.04 (s, 4H, H-4, H-5, H-6, H-7)
7.91 (m, 3H, OH, H-2', H-6')
7.49 (m, 3H, H-3', H-4', H-5')

Example 17

2-Chloracetamido-2-hydroxyindane-1,3-dione 9.62 (s, 1H, NH)
8.04 (s, 4H, H-4, H-5, H-6, H-7)
7.97 (s, 1H, OH)
4.12 (s, 2H, CH2)

2-Benzamido-2-chloroindane-1,3-dione 9.85 (1s, 1H, NH)
8.04 (s, 4H, H-4, H-5, H-6, H-7)
7.90 (m, 2H, H-2', H-6')
7.46 (m, 3H, H-3', H-4', H-5')

Example 18

2-(4-Aminobenzoylhydrazino)-2-hydroxy-indane-1,3-dione 9.53 (1s, 1H, NH)
7.99 (s, 4H, H-4, H-5, H-5, H-7)
7.50 (d, 2H, H-2', H-5', J H2'–3' & 5'–6'=8.3 Hz)
7.40 (s, 1H, OH)
6.53 (d, 2H, H-3, H-5', J H2'–3' & 5'–6'=8.3 Hz)
6.25 (1s, 1H, NH)
5.72 (m, 2H, NH2)

Example 19

2-(4-Aminoethylmorpholino)-2-benzamidoindane-1,3-dione 9.62 (s, 1H, NH)
7.99 (s, 4H, H-4, H-5, H-6, H-7)
7.81 (d, 2H, H-2', H-6', J H2'–3' & 5'–6'=7.8 Hz)
7.50 (m, 3H, H-3', H-4', H-5')
3.50 (m 4H, 2CH2)
3.22 (s, 1H, NH)
2.28 & 2.37 (2m, 8H, 4CH2, morpholino)

Example 20

2-Benzamido-2-[1-(2-pyridyl)-piperazino]indane-1,3-dione 9.46 (s, 1H, NH)
8.08 (m, 1H, H6 pyridine)
8.00 (s, 4H, H-4, H-5, H-6, H-7)
7.87 (d, 2H, H-2', H-6', J H2'–3' & H5'–6'=6.8 Hz)
7.50 (m, 4H, H-3', H-4', H-5', H5 pyridine)
6.75 (d, 1H, H-3 pyridine, J H3–H4'=8.31 Hz)
6.60 (m, 1H, H-4 pyridine)
3.38 (m, 8H, 4CH2, piperazino)

Example 21

2-Benzamido-2-[1-(4-fluorophenyl)-piperazino]indane-1,3-dione 12.00 (s, 1H, NH)
8.00 (s, 4H, H-4, H-5, H-6, H-7)
7.92 (d, 2H, H-2', H-6', J H2'–3' & H5'–6'=7.3 Hz)
7.51 (m, 4H, H-3', H-4', H-5')
6.97.(m, 2H, H-3 & H-5 fluorinated phenyl)
6.85 (m, 2H, H2 & H-6 fluorinated phenyl)
3.00 (m, 8H, 4CH2, piperazino)

Example 22

2-Methoxycarbonylhydrazono-indane-1,3-dione 12.19 (1s, 1H, NH)
7.99 (s, 4H, H-4, H-5, H-6, H-7)
3.86 (s, 3H, CH3)

Example 23

2-Methoxycarbonylhydrazono-5-methoxyindane-1,3-dione 12.19 (1s, 1H, NH)
7.91 (dd, 1H, H-6, J H6–7=8.3 Hz, J H6–4=1.46 Hz)
7.52 (d, 1H, H-7, J H7–6=8.3 Hz.)
7.34 (s, 1H, H-4)
3.97 (s, 3H, CH3)
3.47 (s, 3H, CH3)

Example 24

2-Benzoylhydrazonoindane-1,3-dione 13.60 (1s, 1H, NH)
8.03 (s, 4H, H-4, H-5, H-6, H-7)
7.94 (d, 2H, H-2', H-6', J H2'–3' & H5'–6'=7.8 Hz))
7.66 (m, 3H, H-3', H-4', H-5')

Example 25

2-Benzoylhydrazono-5-methoxyindane-1,3-dione 13.55 (s, 1H, NH)
7.94 (m, 3H, H-4, H-6, H-7)
7.74 (m, 2H, H-2', H-6')
7.66 (m, 3H, H-3', H-4', H-5')
3.98 (s, 3H, OCH3)

2-(2-Methoxybenzoylhydrazono)-indane-1,3-dione 4.26 (s, 1H, NH)
8.12 (d, 1H, H-3', J H3'–4'=7.3 Hz)
8.00 (s ,4H, H-4, H-5,H-6, H-7)
7.70 (m, 1H, H-4')
7.36 (d, 1H, H-6', J H5'–6'=8.3 Hz)
7.18(m, 1H, H-5')
4.21 (s, 3H, OCH3)

2-(3-Methoxybenzoylhydrazono)-indane-1,3-dione 12.3 (s, 1H, NH)
8.00 (s ,4H, H-4, H-5,H-5, H-7)

7.50 (m, 2H, H-2', H4')
7.27 (m, 2H, H-5', H-6')
3.88 (s, 3H, OCH3)

2-(3-Methoxybenzoylhydrazono)-5-methoxyindane-1,3-dione 12.3 (1s, 1H, NH)
7.99 (s, 4H, H-4, H-5, H-6, H-7)
7.33 (m, 3H, H-2', H-3, H-4')
7.11 (s, 1H, H-6')
3.77 (s, 3H, OCH3)

2-(4-Methoxybenzoylhydrazono)-indane-1,3-dione 13.58 (s, 1H, NH)
8.00 (s, 4H, H-4, H-5,H-6, H-7)
7.92 (d, 2H, H-2', H-6'J H2'–3' & H5'–6'=8.7 Hz)
7.18 (d, 2H, H-3', H-5'J H2'–3' & H5'–6'=8.7 Hz)
3.88 (s, 3H, OCH3)

Example 26

2-(2-Methylbenzoylhydrazono)-indane-1,3-dione 13.04 (s, 1H, NH)
8.01 (s ,4H, H-4, H-5,H-6, H-7)
7.57 (m. 2H, H-4', H-5')
7.43 (m, 2H, H-3', H-6')
3.55 (s, 3H, CH3)

Example 27

2-(3-Methylbenzoylhydrazono)-indane-1,3-dione 13.58 (s, 1H, NH)
8.01 (s,4H, H-4, H-5, H-6, H-7)
7.72 (m, 2H, H-2', H-6')
7.53 (m, 2H, H-4', H-5')
3.33 (s, 3H, CH3)

Example 28

2-(4-Methylbenzoylhydrazono)-indane-1,3-dione 13.59 (s, 1H, NH)
8.02 (s ,4H, H-4, H-5,H-6, H-7)
7.84 (d, 2H, H-2', H-6', J H2'–3' & H5'–6'=7.8 Hz)
7.44 (d, 2H, H-3', H-5', J H2'–3' & H5'–6'=7.8 Hz)
3.34 (s, 3H, CH3)

Example 29

2-(2-Hydroxybenzoylhydrazono)-indane-1,3-dione 14.48 (s, 1H, NH)
8.04 (s, 4H, H-4, H-5,H-6, H-7)
7.50 (m, 1H, H-3')
7.05 (m, 3H, H-4', H-5', H-6')

Example 30

2-(3-Hydroxybenzoylhydrazono)-indane-1,3-dione 13,78 (s,1H, NH)
10.17 (s, 1H, OH)
8.04 (s, 4H, H-4, H-5,H-6, H-7)
7.47 (m, 3H, H-2', H-5', H-6')
7.34 (m, 1H, H-4')

Example 31

2-(4-Hydroxybenzoylhydrazono)-indane-1,3-dione 13.58 (s, 1H, NH)
10.62 (s, 1H, OH)
8.01 (s ,4H, H-4, H-5,H-6, H-7)
7.83 (d, 2H, H-2', H-6', J H2'–3' & H5'–6'=8.3 Hz)
7.00 (d, 2H, H-3', H-5', J H2'–3' & H5'–6'=8.3 Hz)

Example 32

2-(3,4-Dihydroxybenzoylhydrazono)-indane-1,3-dione 9.44 (s, 1H, NH)
8.01 (s ,4H, H-4, H-5,H-6, H-7)
7.36 (s, 1H, H-2')
7.25 (d, 1H, H-5', J H5'–6'=8.3 Hz)
6.74 (d, 1H, H-6', J H5'–6'=8.3 Hz)

Example 33

2-(5-Phenyl-2-(N-pyrrolyl)thiophene-3-carbonylhydrazono)-indane-1,3-dione 12.78 (s, 1H, NH)
7.98 (s ,4H, H-4, H-5,H-6, H-7)
7.70 (m, 3H, H2', H6', H thiophene,)
7.44 (m, 3H, H3', H4', H5')
7.12 (s, 2H, H pyrrole)
6.25 (s, 2H, H—N pyrrole)

2-Nicotinoylhydrazonoindane-1,3-dione 13.41 (s, 1H, NH)
9.06 (s, 1H, H-2')
8.85 (d, 1H, H-6', J H5'–6'=4.4 Hz)
8.27 (d, 1H, H-4', J H4'–5'=6.8 Hz)
8.01 (s ,4H, H-4, H-5,H-6, H-7)
7.67 (m, 1H, H-5')

Example 34

2-Oxamoylhydrazonoindane-1,3-dione 13.80 (s, 1H, NH)
8.70 (s, 1H, NH, in DMSO it is in keto-enolic equilibrium)
8.32 (s, 1H, OH, in DMSO it is in keto-enolic equilibrium)
8.02 (s ,4H, H-4, H-5,H-6, H-7)

Example 35

2-(3-Hydroxybenzoylhydrazono)-5-methoxyindane-1,3-dione 13.62 (s, 1H, OH)
10.07 (s, 1H, NH)
8.00 (d, 1H, H-6, J H6–7=8.3 Hz)
7.95 (m, 6H, H-4, H-5, H-7, H-2', H-4', H5')
7.32 (d, 1H, H-6', J H5'–6'=8.2 Hz)
4.01 (s, 3H, CH3)

Example 36

2-(3,4-Dimethoxybenzoylhydrazono)-indane-1,3-dione 12.3 (1s, 1H, NH)
8.00 (s, 4H, H-4, H-5, H-6, H-7)
7.35 (m, 3H, H-2', H-5', H-6')
3.78 et 3.79 (2s, 6H, CH3O)

Example 37

2-(2-Hydroxy-3-methylbenzoylhydrazono)-indane-1,3-dione 14.51 (s, 1H, NH)
11.08 (s, 1H, OH)

8.08 (s, 4H, H-4, H-5, H-6, H-7)
7.85 (d, 1H, H-6', J H5'–6'=7.8 Hz)
7.42 (d, 1H, H-4', J H4'–5'=7.3 Hz)
6.95 (m, 1H, H-5')
2.30 (s, 3H, CH3)

Example 38

2-(4-Hydroxy-3-methoxybenzoylhydrazono)-indane-1,3-dione 14.51 (s, 1H, NH)
11.08 (s, 1H, OH)
8.01 (m, 4H, H-4, H-5, H-6, H-7)
7.50 (s, 1H, H-2')
7.43 (d, 1H, H-6', J H5'–6'=8.3 Hz)
7.00 (d, 1H, H-5', J H5'–6'=8.3 Hz)
3.88 (s, 3H, CH3)

Isonicotinoylhydrazino-indane-1,3-dione 13.47 (1s, 1H, NH)
8.90 (d, 2H, H-3', H-5', J H2'–3' & JH5'–6'=6.35 Hz)
8.03 (s, 4H, H-4, H-5, H-6, H-7)
7.81 (m, 2H, H-2', H-6', J H2'–3' & JH5'–6'=6.35 Hz)

2-Isonicotinoylhydrazono-5-methoxyindane-1,3-dione 13.47 (s, 1H, NH)
8.73 (d, 2H, H-3', H-5', J H2'–3' & 5'–6'=5.8 Hz)
7.94 (d, 1H, H-7, J H6–7=8.8 Hz)
7.69 (d,2H, H-2', H-6', J H2'–3' & 5'–6'=5.8 Hz)
7.45 (dd, 1H, H-6,, J H4–6=2.4 & 6–7=8.8 Hz)
7.41 (d, 1H, H-4, J H4–6=2.4 Hz)
3.38 (s,3H, CH3)

Example 39

2-(2-Thenoylhydrazono)-indane-1,3-dione 13.09 (1s, 1H, NH)
8.13 (d, 1H, H-3', J H3'–4'=4.9 Hz)
8.05 (m, 1H, H-5')
8.02 (s, 4H, H-4, H-5, H-6, H-7)
34 (t, 1H, H-4', J H3'–4' & J H4'–5'=4.9 Hz)

Example 40

2-(2-Furoylhydrazono)-indane-1,3-dione 13.49 (1s, 1H, NH)
8.13 (1s, 1H, H-3')
8.01 (s, 4H, H-4, H-5, H-6, H-7)
7.56 (m, 1H, H-5')
6.85 (m, 1H, H-4')

Example 41

2-(4-Aminobenzoylhydrazono)-indane-1,3-dione 13.61 (1s, 1H, NH)
8.00 (s, 4H, H-4, H-5, H-6, H-7)
7.67 (d, 2H, H-2', H-6', J H2'–3' & J H5'–6'=8.3 Hz)
6.71 (d, 2H, H-3, H-5', J H2'–3' & J H5'–6'=8.3 Hz)
6.30 (1s, 2H, NH2)

Example 42

2-(4-Trifluoroacetylaminobenzoylhydrazono)-indane-1,3-dione 13.58 (1s, 1H, NH)
11.68 (1s, 1H, NH)
8.00 (s, 4H, H-4, H-5, H-6, H-7)
7.96 (s, 4H, Phe)

Example 43

2-(4-Acetylaminobenzoylhydrazono)-indane-1,3-dione 13.56 (1s, 1H, NH)
10.38 (1s, 1H, NH)
8.00 (s, 4H, H-4, H-5, H-6, H-7)
7.83 (m, 4H, Phe)
2.08 (s, 3H, CH3)

2-Phenylhydrazonoindane-1,3-dione 13.16 (1s, 1H, NH)
7.89 (s, 4H, H-4, H-5, H-6, H-7)
7.63 (d, 2H, H-2', H-6', J H2'–3' & J H5'–6'=8.1 Hz)
7.46 (t, 2H, H-3', H-5', J H2'–3' & J H5'–6'=8.1 Hz)
7.24 (m, 1H, H-4')

Example 50

2-(2,4-Dichlorophenylhydrazono)-indane-1,3-dione 12.64 (1s, 1H, NH)
7.96 (s, 4H, H-4, H-5, H-6, H-7)
7.66 (s, 1H, H-3')
7.44 (d, 2H, H-5', H-6', J H5'–6'=8.8 Hz)

Example 51

2-(3-Chloro-4-methylphenylhydrazono)-indane-1,3-dione 13.01 (1s, 1H, NH)
7.87 (s, 4H, H-4, H-5, H-6, H-7)
7.65 (s, 1H, H-2')
7.45 (m, 2H, H-5', H-6')
2.27 (s, 3H, CH3)

2-(3-Fluorophenylhydrazono)-indane-1,3-dione 13.05 (1s, 1H, NH)
7.90 (s, 4H, H-4, H-5, H-6, H-7)
7.47 (m, 3H, H-2', H-4', H-6')
7.01 (m, 1H, H-5')

2-(3-Fluorophenylhydrazono)-5-methoxyindane-1,3-dione 12.94 (1s, 1H, NH)
7.89 (d, 1H, H7, J H6–7=8.3 Hz)
7.97 (m, 5H, H4, H-6, H-2', H-4', H-6')
7.31 (m, 1H, H-5')
3.95 (s, 3H, OCH3)

2-(4-Fluorophenylhydrazono)-indane-1,3-dione 13.56 (1s, 1H, NH)
7.88 (s, 4H, H-4, H-5, H-6, H-7)
7.76 (m, 2H, H-3', H-5')
7.63 (m, 2H, H-2', H-6')

2-(3-Methylphenylhydrazono)-indane-1,3-dione 13.11 (1s, 1H, NH)
7.85 (s, 4H, H-4, H-5, H-6, H-7)
7.35 (m, 3H, H-2', H-5', H-6')

7.00 (d, 1H, H-4', J H4'–5'=6.8 Hz)
3.38 (s, 3H, CH3)

2-(4-Methoxyphenylhydrazono)-indane-1,3-dione 13.28 (1s, 1H, NH)
7.85 (s, 4H, H-4, H-5, H-6, H-7)
7.58 (d, 2H, H-2', H-6', J H2'–3' & J H5'–6'=8.8 Hz)
7.02 (d, 2H, H-3, H-5', J H2'–3' & J H5'–6'=8.3 Hz)
3.77 (s, 3H, OCH3)

2-(4-Methoxyphenylhydrazono)-5-methoxyindane-1,3-dione 13.12 (1s, 1H, NH)
7.77 (d, 1H, H-7, J H6–H7=83 Hz)
7.53 (d, 2H, H-2', H-6', J H2'–3' & 1 H5'–6'=8.8 Hz)
7.34 (m, 2H, H-4, H-6)
7.00 (d, 2H, H-3', H-5', J H2'–3' & J H5'–6'=8.8 Hz)
3.77 (s, 3H, OCH3)

Example 52

2-(4-methylsulfonylphenylhydrazono)-indane-1,3-dione 13.73 (1s, 1H, NH)
7.80 (m, 8H, H-4, H-5, H-6, H-7, H-2', H-3, H-5', H-6')
3.22 (s, 3H, OCH3)

Example 53

5-Hydroxy-2-(4-methylsulfonylphenylhydrazono)-indane-1,3-dione 12.93 (1s, 1H, NH)
1.16 (1s, 1H, OH)
7.78 (d, 2H,, H-3, H-5', J H2'–3' & J H5'–6'=7.8 Hz)
7.20 (m, 3H, H-6, H-2', H-6')
7.21 (d, 1H, H-7, J H6–7=8.3 Hz)
7.15 (s, 1H, H-4)
3.23 (s, 3H, OCH3)

Example 54

2-(4-N-Methylmethanesutfonamidophenylhydrazono)-indane-1,3-dione 13.17 (1s, 1H, NH)
7.88 (s, 1H, H-4, H-5, H-6, H-7)
7.63 (d, 2H, H-2', H-6', J H2'–3' & J H5'–6'=8.8 Hz)
7.42 (d, 2H, H-3, H-5', J H2'–3' =8, J H5'–6'=8.8 Hz)
6.96 (d, 1H, NH, J NH—CH3=4.4 Hz)
4.34 (s, 2H, CH2)
2.56 (d, 3H, CH3, J NH—CH3=4.4 Hz)

Example 55

5-Methoxy-2-(4-N-methylmethanesulfonamidophenylhydrazono)-indane-1,3-dione 13.04 (1s, 1H, NH)
7.82 (d, 1H, H-7J, J H6–7=8.3 Hz)
7.58 (d, 2H, H-2', H-6', J H2'–3' & J H5'–6'=8.3 Hz)
7.42 (d, 2H, H-3', H-5', J H2'–3' & J H5'–6'=8.3 Hz)
7.38 (m, 2H, H-4, H-6)
6.95 (d, 1H, NH, J NH—CH3=4.9 Hz)
4.33 (s, 2H, CH2)
3.38 (s, 3H, CH3O)
2.58 (d, 3H, CH3, J NH—CH3=4.9 Hz)

Example 56

2-(2-Hydroxyphenyl)-iminoindane-1,3-dione 8.00 (s, 4H, H-4, H-5, H-6, H-7)
7.85 (m, 4H, H-3', H-4', H-5', H-6')

Example 62

2-Oximino-1-(4-phenylthiosemicarbazono)-3-indanone 9.40 (1s, 1H, OH)
9.30 (1s, 1H, NH)
8.36 (d, 1H, H-7, J H6–7=7.3 Hz)
7.73 (m, 5H, H-4, H-5, H-6, H-2', H-6')
7.31 (t, 2H, H-3, H-5', J H2'–3' & J H5'–6'=7.3 Hz)
7.06 (t, 1H, H-4', J H3'–4' & JH4'–5'=7.3 Hz)

Example 63

1,3-Dioximino-2-(4-phenylthiosemicarbazono)-3-indanone 13.05 (1s, 1H, NH)
12.59 (1s, 1H, OH)
11.63 (1s, 1H, OH)
9.19 (1s, 1H, NH)
8.56 (d, 1H, H-7, H-4, J H6–7 & J H4–5=7.3 Hz)
7.64 (m, 4H, H-5, H-6, H-2', H-6')
7.33 (t, 2H, H-3', H-5', J H2'–3' & 1H5'–6'=7.3 Hz)
7.03 (t, 1H, H-4', J H3'–4' & JH4'–5'=7.3 Hz)

The invention also covers use in human and veterinary therapy on the one hand of the compounds having the formula:

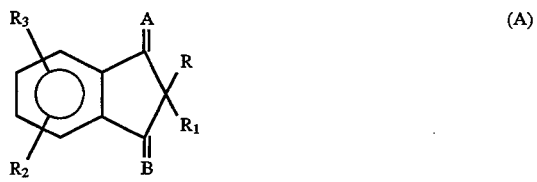

(A)

in which $R_2$ and $R_3$ independently denotes H, $C_1$–$C_4$ alkoxy or OH, and the pair (A, B) denotes either:

(oxygen, oxygen), in which case one out of R and $R_1$ denotes OH, halogen, ($C_1$–$C_4$ alkyl) NH, N-morpholino($C_1$–$C_4$ alkyl) NH, 1-(pyridyl)-4-piperazino or 1-(phenyl)-4-piperazino in which the phenyl ring is optionally substituted by a halogen, and the other denotes a group chosen from among the following:

NHCOR$_4$ where R$_4$=phenyl, $C_1$–$C_4$ alkyl or $C_1$–$C_4$ alkyl substituted by a halogen, NHNHCOR$_5$ where R$_5$=$C_1$–$C_4$ alkoxy; phenyl, phenyl substituted by one ot two groups chosen from among the following: amino, $C_1$–$C_4$ alkoxy, $C_1$–$C_4$ alkyl or OH; thienyl; furyl; pyridyl; indolyl-2-methyl, indolyl-3-methyl; or 5-phenyl-2-(N-pyrrolyl)thienyl, or

NHNHCOCONH$_2$,

R and $R_1$ may also together form a group, i.e.:
=NNHCOR'$_5$ where R'$_5$=R$_5$, trifluoroacetyl aminophenyl, acetyl aminophenyl, pyrazinyl or pyrrolyl, =NNHCOCONH$_2$,
=NNHR$_6$ where R$_6$=phenyl; phenyl substituted by one or two groups chosen from among $C_1$–$C_4$ alkyl, halogen and $C_1$-$C_4$ alkoxy; methyl sulphonyl phenyl; or N-methyl methane sulphonamidophenyl, =N—$R_7$ where $R_7$=phenyl or phenyl substituted by an OH group, =N—O—CO—$R_8$ where $R_8$=phenyl or phenyl substituted by a halogen atom or =C($CH_3$)—NH—NH—CO—$R_9$ where $R_9$=phenyl, phenyl amino, phenyl substituted by a halogen atom or an OH group, or phenylamino substituted by a halogen atom or an OH group, or (NNHCXNH$R_{10}$, oxygen) where X denotes oxygen or sulphur and $R_{10}$=H, phenyl or phenyl substituted by one or two groups chosen from among OH, $CF_3$, $C_1$-$C_4$ alkyl, $C_1$-$C_4$ alkoxy, halogen, methylene dioxy, acetoxy and hydroxyethyl, in which case R and $R_1$ together form an =N—OH group, except for compounds in which R and $R_1$ together form an =N—NH—CO—R'$_5$ group where R'$_5$=pyridyl;

and on the other hand pharmaceutically acceptable mineral or organic acid addition salts of the salt-forming compounds among those having the formula (A) hereinbefore.

The formula (A) compounds and their salts, if any, not included in formula (I) are known and can be prepared in accordance with diagrams ① to ⑤ hereinbefore, using the appropriate starting products.

A study of the formula (A) and their salts, if any, has shown that they have various pharmacological properties. For example they are venotonic and in most cases do not affect the arterial system. They also increase the capillary resistance, reduce vascular hyperpermeability induced by certain inflammatory agents and have antilipoperoxidising, antiradical and anti-inflammatory properties and activity in septic shock.

These properties are shown in mammals such as rats, guinea-pigs and rabbits, under in vitro (isolated vessels or vascular networks) and in vivo conditions.

In the in vitro test, the compounds were solubilised in aqueous solution, either pure or containing DMSO or alcohol.

In the in vivo test, the products were administered intravenously in the form of a pure aqueous solution or intraperitoneally in the form of an aqueous solution optionally containing DMSO or orally in solution or in suspension in carboxymethyl cellulose or in a composite aqueous solution containing Tween® and DMSO in certain cases.

Pharmacological study models

The contractile effect was measured in vitro:
by the contractile force exerted by vascular rings, either quiescent or stimulated (electrically or by physiological agents) and maintained under isometric conditions, and
by the pressure exerted by vascular networks perfused at a constant flow rate.

In vivo, the arterial and venous pressure was measured under normal conditions and after cardiac arrest. During cardiac arrest, the venous tone was calculated from the venous and arterial pressure measured at equilibrium and corrected in dependence on the relative differences in compliance between these two networks (Samar and Coleman, Am. J. Physiol., 1978, 234:H94–100; Yamamoto et al., Am. J. Physiol., 1980, 238:H823–828).

The increase in capillary resistance was estimated by modification of the petechial index (negative pressure inducing extravasation of erythrocytes) measured by a method derived from the Parrot angiosterrometer.

The vascular permeability was studied in vivo and in vitro by measuring the extravasation of albumin or dye binding the albumin (Evans Blue). In vivo, hyperpermeability was induced by injection of a solution of histamine, bradykinin or zymosan. The in vitro models were used to obtain hyperpressure (over an isolated vascular region) and/or inflammatory vascular reactions.

The anti-inflammatory activity was demonstrated by measuring the inhibition of oedema and leucocyte migration after induction of pleurisy in the rat by injection of carrageenin into the pleural cavity (Almeida et al., J. Pharmacol. Exp. Therap., 1980, 214:74).

The overall "free radical trapping" effect was studied in vitro in a model using 1,1-diphenyl-2-picrylhydrazyl (DPPH) as stable free radical, the method being derived from that described by Lamaison et al., Plantes Médic. et phytothéraphie, XXII, 1988, 231–234.

The anti-oxidising activity was studied in vitro using a lipid peroxidation model based on peroxidation of an emulsion of linoleic acid by iron, the method being a modification of that described by Sutherland et al., Arch. Biochem. Biophys. 1982, 214, 1–11.

The activity in septic shock was studied in the rat after induction by a lipopolysaccharide endotoxin (15 mg/kg), the method being similar to that described by Terashita et al., Eur. J. Pharmacol., 109, 257–261, 1985.

Examples of pharmacological effects

The formula (A) compounds and their salts, if any, increase the contraction of animal saphena veins produced by noradrenalin and depolarisation (hyperpotassic solution) without in most cases affecting the arterial contractile responses. For example, 2-hydroxy-2-(2-methoxybenzoyl hydrazino)-indan-1,3-dione and the compound in Example 22 (10 nM to 30 µM) produce a more than 50% increase ($ED_{50}$±0.3 microM) in contractions of the saphena veins of rabbits produced by KCl (40 mM).

The compounds in Examples 3 and 12 and 2-(3-methylphenyl hydrazono)-indan-1,3-dione at their maximum concentration increases by 30 to 200% the contraction of the saphena veins in the rabbit in response to 0.3 micromolar noradrenalin.

The compounds in Examples 3, 6 and 11 produce a more than 20% increase in the basic venous tone of the rat without affecting the arterial pressure at doses of 1 to 3 picomols administered intravenously.

By way of illustration, the compounds in Examples 17, 22 and 54 and 2-isonicotinoyl hydrazonoindan-1,3-dione increase the basic capillary resistance by 10 to 100%, when measured one to two hours after administration of 5–20 mg/kg intraperitoneally and up to 4 to 6 hours after oral administration of 5–20 mg/kg to the rat.

The compounds in Examples 1, 3 and 11 and 2-hydroxy-2-(3-methoxybenzoyl hydrazino)-indan-1,3-dione reduce vascular permeability by 10 to 50% when measured one to two hours after intraperitoneal administration of 5–20 mg/kg and 2 to 4 hours after oral administration of 5–20 mg/kg to the rat. The compound in Example 9 and 2-isonicotinoyl hydrazonoindan-1,3-dione, administered intraperitoneally twice in doses of 20 mg/kg, inhibit oedema and leucocyte migration in the pleural cavity, six hours after injection of carrageenin in the model of pleurisy in the rat.

The compounds in Examples 9 and 56 and 2-(3-fluorophenyl hydrazono)-5-methoxyindan-1,3-dione have a maximum anti-radical effect of more than 95% in the model using DPPH.

Toxicity

The formula (A) compounds and their salts if any have very low toxicity. For example after a single oral administration to the mouse, no deaths were observed at a dose of 1 g/kg of 2-phenyl hydrazonoindan-1,3-dione. The only observed effects, in certain cases, were coloured diarrhoea and coloured urine, the latter being evidence of resorption of the product.

As the preceding shows, the formula (A) compounds and their salts if any can be used in human and animal therapy. They are particularly indicated, with regard to their vascular and anti-inflammatory components, in functional, organic venous insufficiency and morbid haemorrhoid states and in typically inflammatory complaints (osteo-articular, dermatological or cardiovascular) and in states of shock consisting of a considerable drop in arterial pressure, more particularly in states of septic (endotoxic) shock.

Functional venous insufficiency is characterised by dilation and hyperdistensibility of the surface veins of the lower limbs accompanied by functional symptoms, i.e. pain in the lower limbs, oedema, and paraesthesia, e.g. tingling and fidgety legs. This morbid state may develop into organic venous insufficiency (varicose veins, deep valvular incontinence, etc) or into phlebo-thrombosis or ulcerous lesions.

In these venous states, an inflammatory component appears in the first stages and is shown more clearly in the advanced stages.

The invention therefore comprises use of the aforementioned formula (A) and their salts, if any, as active substances in the preparation of drugs and pharmaceutical compositions for human or veterinary use and comprising at least one of the aforementioned compounds or salts in association with a physiologically acceptable excipient or diluent.

The form of the drugs and pharmaceutical compositions will of course depend on the desired method of administration, inter alia oral, parenteral or rectal, and the drugs can be formulated by conventional methods with usual excipients and vehicles.

For example in the case of oral administration, the drugs can be in the form of pills, tablets, capsules, solutions, syrups or suspensions.

The pills, tablets and capsules contain the active substance together with a diluent (e.g. lactose, dextrose, sucrose, mannitol, sorbitol or cellulose), a lubricant (e.g. silica, talc or stearate, e.g. magnesium stearate), a binder (e.g. starch, methyl cellulose or gum arabic) and a disintegrating agent (e.g. alginate) and are manufactured by known methods such as mixing, granulation, pelleting or coating.

The excipient in syrups can be glycerol, mannitol and/or sorbitol. The solutions and suspensions can contain water and an excipient such as a natural gum or gelose or sodium alginate or polyvinyl alcohol.

For parenteral administration, the drugs or composition can be in the form of solutions, emulsions or suspensions containing the active substance and a suitable excipient such as sterile water or sterile aqueous isotonic saline solutions.

For rectal administration, they can be in the form of suppositories containing the active substance and a suitable excipient such as cocoa butter or polyethylene glycol.

The therapeutic dose of the active substances can be up to 1000 mg per day, depending on the method of administration, the age, weight and state of the patient, and the therapeutic power of the active substance.

We claim:

1. Indan compounds of the formula:

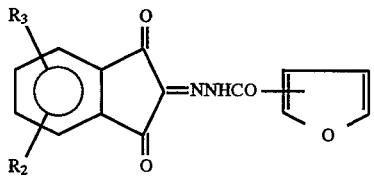

where $R_2$ and $R_3$ each independently represent H, $C_1$–$C_4$ alkoxy or OH.

2. A method for the treatment of functional organic venous insufficiency, morbid hemorrhoid, inflammatory complaints, shock consisting of a considerable drop in arterial pressure and septic shock, in human or animal, which comprises administering to a human or animal in need of such a treatment an effective amount of an indan compound or a pharmaceutically acceptable salt of an indan compound of the formula:

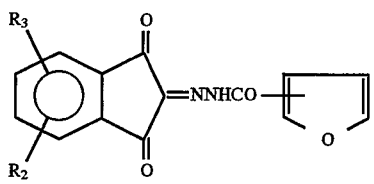

where $R_2$ and $R_3$ each independently represent H, $C_1$–$C_4$ alkoxy or OH.

3. A pharmaceutical composition comprising a physiologically acceptable excipient or diluent and at least one indan compound or pharmaceutically acceptable salt of an indan compound of the formula:

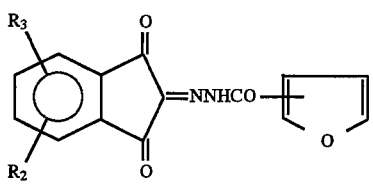

where $R_2$ and $R_3$ each independently represent H, $C_1$–$C_4$ alkoxy or OH.

4. A method for preparing compounds of claim 1, comprising heating a compound of the formula:

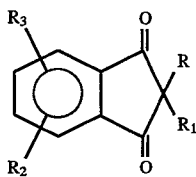

wherein one out of R and $R_1$ is OH and the other is NH—NH—CO—furyl, in ethanol in the presence of concentrated HCl or in acetonitrile.

5. A method for preparing compounds of claim 1, comprising hot condensation of $H_2N$—NH—CO—furyl on indan-1,2,3,-trione monohydrate having the formula:

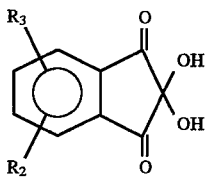

* * * * *